US012583841B2

(12) United States Patent
Wei et al.

(10) Patent No.: US 12,583,841 B2
(45) Date of Patent: Mar. 24, 2026

(54) TETRAHYDROPYRROLOCYCLIC COMPOUND AND APPLICATION THEREOF

(71) Applicant: Breakthrough Pharmaceuticals Inc., Jiangsu Province (CN)

(72) Inventors: Wei Wei, Shanghai (CN); Peng Li, Shanghai (CN); Na Gao, Shanghai (CN); Haiying He, Shanghai (CN); Jian Li, Shanghai (CN); Shuhui Chen, Shanghai (CN)

(73) Assignee: Breakthrough Pharmaceuticals Inc., Jiangsu Province (CN)

( * ) Notice: Subject to any disclaimer, the term of this patent is extended or adjusted under 35 U.S.C. 154(b) by 327 days.

(21) Appl. No.: 18/275,251

(22) PCT Filed: Jan. 27, 2022

(86) PCT No.: PCT/CN2022/074381
§ 371 (c)(1),
(2) Date: Aug. 1, 2023

(87) PCT Pub. No.: WO2022/166768
PCT Pub. Date: Aug. 11, 2022

(65) Prior Publication Data

US 2024/0300925 A1 Sep. 12, 2024

(30) Foreign Application Priority Data

Feb. 2, 2021 (CN) ......................... 202110146135.9
Jun. 2, 2021 (CN) ......................... 202110617562.0
Aug. 11, 2021 (CN) ......................... 202110906535.5
Dec. 27, 2021 (CN) ......................... 202111625215.9

(51) Int. Cl.
*C07D 403/14* (2006.01)
*A61K 31/4192* (2006.01)
*A61K 31/506* (2006.01)
*A61P 25/20* (2006.01)
*A61P 25/24* (2006.01)

(52) U.S. Cl.
CPC ........ *C07D 403/14* (2013.01); *A61K 31/4192* (2013.01); *A61K 31/506* (2013.01); *A61P 25/20* (2018.01)

(58) Field of Classification Search
CPC ......................... C07D 403/14; A61K 31/4192; A61K 31/506; A61P 25/20; A61P 25/24
See application file for complete search history.

(56) References Cited

U.S. PATENT DOCUMENTS 8,030,495 B2 * 10/2011 Coleman ............. C07D 417/14 548/200
2010/0016401 A1 1/2010 Aissaoui et al.
2010/0152191 A1 6/2010 Coleman et al.
2011/0124636 A1 5/2011 Aissaoui et al.
2015/0166527 A1 6/2015 Boss et al.
2016/0368901 A1 12/2016 Boss et al.
2017/0001985 A1 1/2017 Boss et al.

FOREIGN PATENT DOCUMENTS

CN 104334544 A 2/2015
CN 105793257 A 7/2016
CN 105873921 A 8/2016
JP 2009016560 A 1/2009
JP 2010504957 A 2/2010
JP 2010514751 A 5/2010
JP 2010528007 A 8/2010
JP 2010534646 A 11/2010
WO 2014057435 A1 4/2014
WO WO-2020007964 A1 * 1/2020 ........... C07D 403/14

OTHER PUBLICATIONS

Aug. 28, 2024 Japanese Search Report issued in Japanses Patent Application No. 2023- 547113.
Aug. 28, 2024 Notice of Reasons for Refusal of the Japanese Searching Authority issued in Japanese Patent Application No. 2023-547113.
Sep. 11, 2024 Written Opinion of the Canadian Intellectual Property Office issued in Canadian Patent Application No. 3,206,870.
Apr. 28, 2022 International Search Report issued in International Patent Application No. PCT/CN2022/074381.
Apr. 28, 2022 Written Opinion of the International Searching Authority issued in International Patent Application No. PCT/CN2022/074381.
C. Peyron, et. al. “Neurons Containing Hypocretin (Orexin) Project to Multiple Neuronal Systems”, J. Neurosci., 1998, 18(23), 9996-10015.
T. Sakurai, “The neural circuit of orexin (hypocretin): maintaining sleep and wakefulness”, Nature Reviews Neuroscience, 2007, 8(3), 171-181.

(Continued)

*Primary Examiner* — Kamal A Saeed
*Assistant Examiner* — Sagar Patel
(74) *Attorney, Agent, or Firm* — Harness, Dickey & Pierce, P.L.C.

(57) ABSTRACT

A tetrahydropyrrolocyclic compound as represented by formula (I), a pharmaceutically acceptable salt thereof, and an application thereof in preparation of a drug for treating a disease related to a selective orexin-2 (OX-2) receptor antagonist, wherein the related disease is selected from insomnia and depression.

(I)

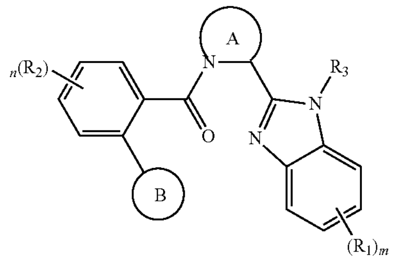

11 Claims, No Drawings

(56) References Cited

OTHER PUBLICATIONS

Piper et. al. J. "The novel brain neuropeptide, orexin-A, modulates the sleep-wake cycle of rats", Neurosci. 2000, 12, 726-730.
Lin et. al. "The Sleep Disorder Canine Narcolepsy Is Caused by a Mutation in the Hypocretin (Orexin) Receptor 2 Gene", Cell 1999,98,365-376.
Nishino et. al. "Hypocretin (orexin) deficiency in human narcolepsy", Lancet 2000, 355, 39-40.
Feb. 11, 2025 Extended supplementary search report and opinion issued in European Patent Application No. 22749047.1.
Mar. 18, 2025 First Office Action issued in Chinese Patent Application No. 202280012699.6.
Boss Christoph et al: "The Quest for the Best Dual Orexin Receptor Antagonist (Daridorexant) for the Treatment of Insomnia Disorders", Chemmedchem Communications, vol. 15, No. 23, Oct. 28, 2020 (Oct. 28, 2020), pp. 2286-2305.
Apr. 27, 2025 First Office Action issued in Malaysia Patent Application No. PI2023004609.
May 29, 2025 Second Office Action issued in Chinese Patent Application No. 202280012699.6.

* cited by examiner

TETRAHYDROPYRROLOCYCLIC COMPOUND AND APPLICATION THEREOF

CROSS-REFERENCE TO RELATED APPLICATIONS

The present application is a U.S. National Phase Application under 35 U.S.C. 371 of International Application No. PCT/CN2022/074381, which claims the right of priorities of Chinese patent application numbers CN 2021101461359 with application date of Feb. 2, 2021; CN 2021106175620 with application date of Jun. 2, 2021; CN 2021109065355 with application date of Aug. 11, 2021; and CN 2021116252159 with application date of Dec. 27, 2021. The entire disclosures of the aforementioned Chinese patent applications are incorporated herein by reference.

TECHNICAL FIELD

The present disclosure relates to a class of tetrahydropyrrolocyclic compounds, in particular to compounds represented by formula (I) and pharmaceutically acceptable salts thereof.

BACKGROUND

Orexin (Hypocretin) signaling is mediated by two receptors and two peptide agonists. Specifically, orexin A and orexin B bind to two high affinity receptors, called the orexin-1 receptor (OX-1 receptor) and the orexin-2 receptor (OX-2 receptor). The OX-1 receptor binds to orexin A with a higher affinity, while the OX-2 receptor binds to orexin A and orexin B with similar affinity. Orexin-secreting neurons are mainly distributed in the prefrontal nucleus, dorsal hypothalamus and lateral hypothalamus (C. Peyron et al., J. Neurosci., 1998, 18(23), 9996-10015). The secreted orexin affects many areas of the brain and is involved in many behavioral and physiological functions, including: eating, drinking, reproduction, arousal system, stress system, reward system, etc. (T. Sakurai, Nature Reviews Neuroscience, 2007, 8(3), 171-181). Among them, the orexin system has a significant regulatory effect on the sleep-wake process, and the awake time of rodents administered with orexin intraperitoneally is prolonged (Piper et al., J. Neurosci. 2000, 12, 726-730). On the other hand, mutant or non-functional orexin-2 receptors would cause narcolepsy in dogs (Lin et al., Cell, 1999, 98, 365-376) and the orexin signal in cerebrospinal fluid of individual with narcolepsy is found deficient (Nishino et al., Lancet 2000, 355, 39-40). All this shows that the orexin system promotes wakefulness of humans, while the inhibition of the orexin system facilitates sleep. Therefore, orexin receptor antagonists are useful in the treatment of the following diseases: insomnia, depression, anxiety, drug addiction, mental disorders, dementia, schizophrenia, Parkinson's disease, Alzheimer's disease, insulin resistance, type II diabetes, hyperlipidemia, gallstones, angina, high blood pressure, dyspnea, tachycardia, infertility, sleep apnea, back and joint pain, varicose veins, osteoarthritis, etc.

CONTENT OF THE PRESENT INVENTION

The present disclosure provides a compound represented by the following formula or a pharmaceutically acceptable salt thereof, which is selected from:

(I)

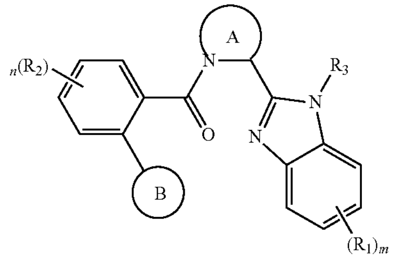

wherein each $R_1$ is independently selected from halogen, cyano, $C_{1-3}$alkyl and $C_{1-3}$alkoxy, and the $C_{1-3}$alkyl and $C_{1-3}$alkoxy are each independently and optionally substituted by 1, 2 or 3 halogen atoms;

each $R_2$ is independently selected from halogen, cyano, $C_{1-3}$alkyl and $C_{1-3}$alkoxy, and the $C_{1-3}$alkyl and $C_{1-3}$alkoxy are each independently and optionally substituted by 1, 2 or 3 halogen atoms;

$R_3$ is selected from H, $C_{1-3}$alkyl and $C_{3-6}$cycloalkyl;

m and n are each independently selected from 0, 1, 2 and 3;

ring A is selected from

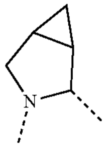 and 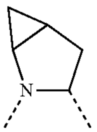;

ring B is selected from

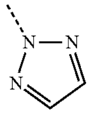, 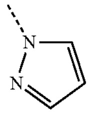, 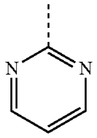 and 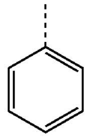.

In some embodiments of the present disclosure, each $R_1$ described above is independently selected from halogen, cyano, methyl and methoxy, and the methyl and methoxy are independently and optionally substituted by 1, 2 or 3 F, and other variables are as defined in the present disclosure.

In some embodiments of the present disclosure, each $R_1$ described above is independently selected from F, Cl, methyl and methoxy, and other variables are as defined in the present disclosure.

In some embodiments of the present disclosure, each $R_2$ described above is independently selected from halogen, cyano, methyl and methoxy, and the methyl and methoxy are each independently and optionally substituted by 1, 2 or 3 F, and other variables are as defined in the present disclosure.

In some embodiments of the present disclosure, each $R_2$ described above is independently selected from F, Cl, methyl and methoxy, and other variables are as defined in the present disclosure.

In some embodiments of the present disclosure, $R_3$ described above is selected from H, methyl and cyclopropyl, and other variables are as defined in the present disclosure.

In some embodiments of the present disclosure, the compounds described above are selected from the structures represented by formulas (I-1), (I-2) and (I-3):

(I-1)

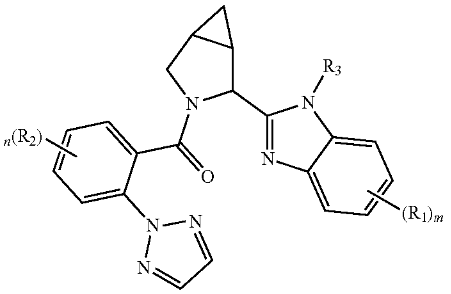

(I-2)

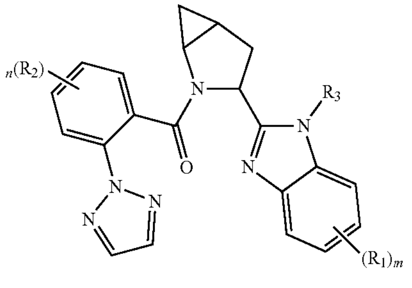

(I-3)

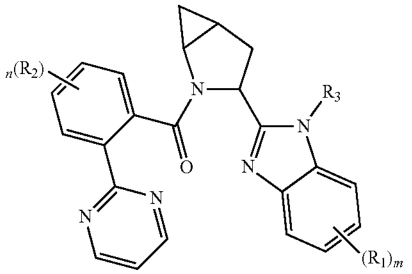

wherein $R_1$, $R_2$, $R_3$, m and n are as defined in the present disclosure.

There are still some embodiments of the present disclosure derived from any combination of the above-mentioned variables.

The present disclosure further provides the following compound or a pharmaceutically acceptable salt thereof, wherein the compound is selected from:

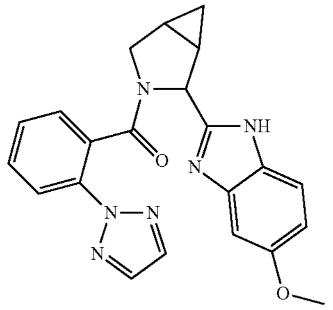

-continued

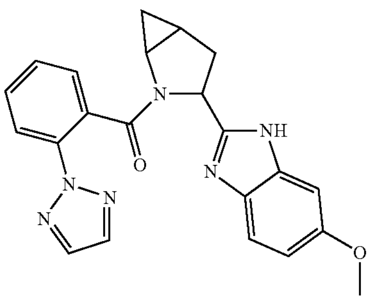

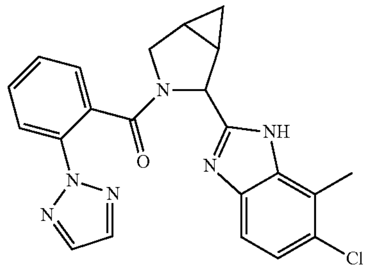

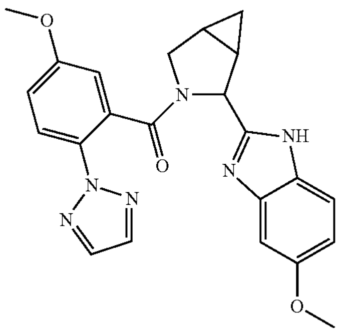

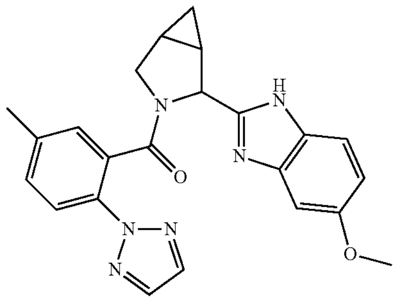

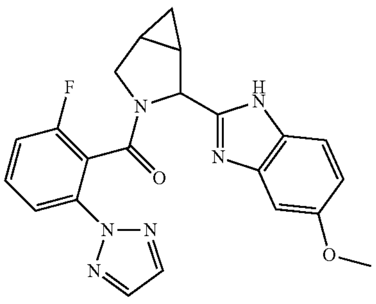

-continued
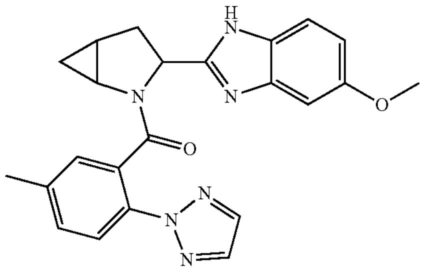
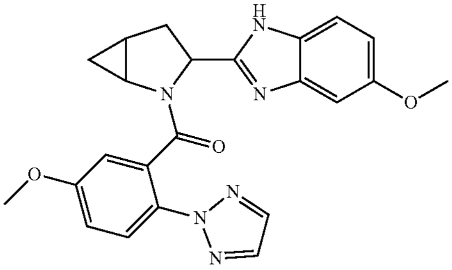
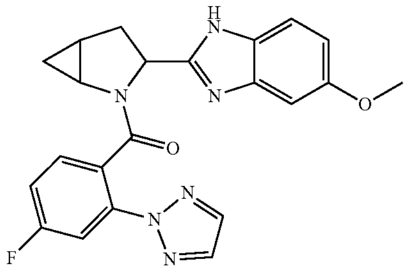
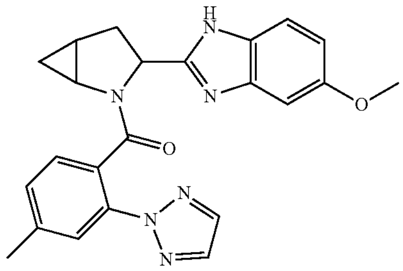
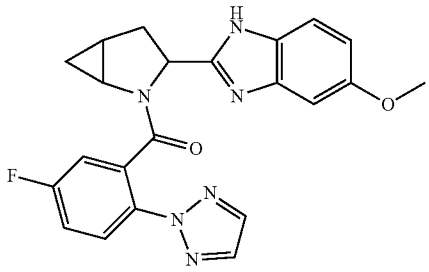
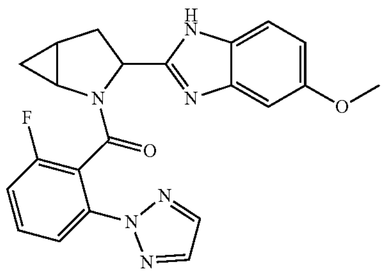
-continued
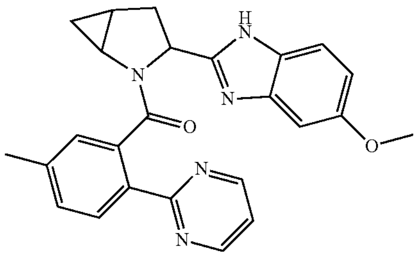
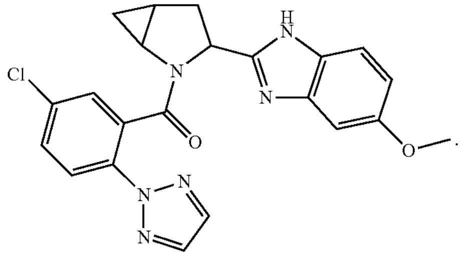
In some embodiments of the present disclosure, for the compound or the pharmaceutically acceptable salt thereof described above, wherein the compound is selected from:
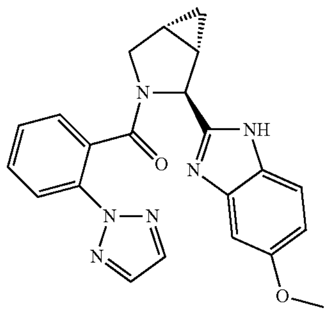
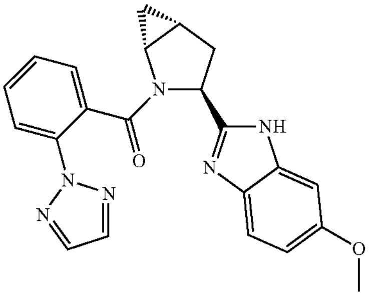
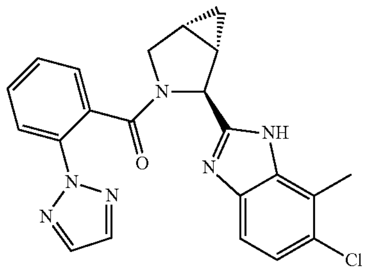

-continued

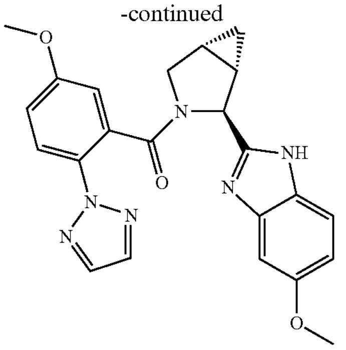

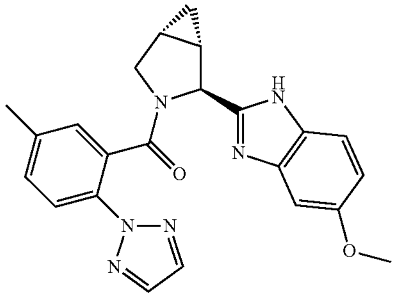

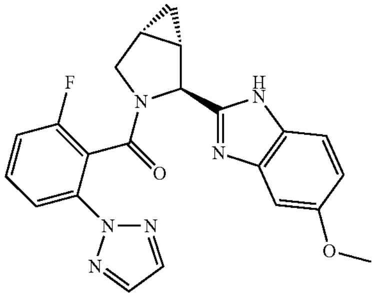

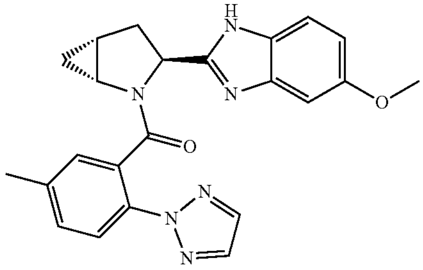

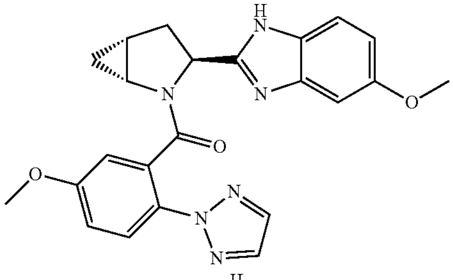

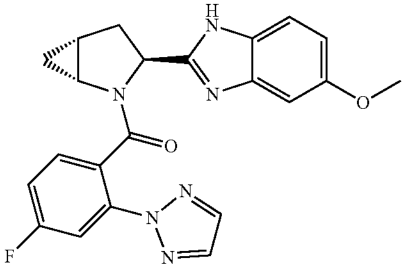

-continued

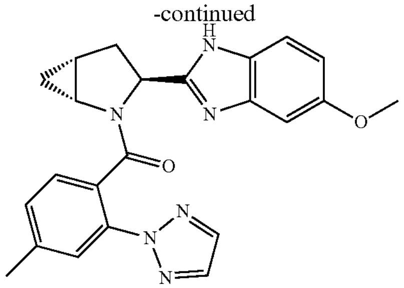

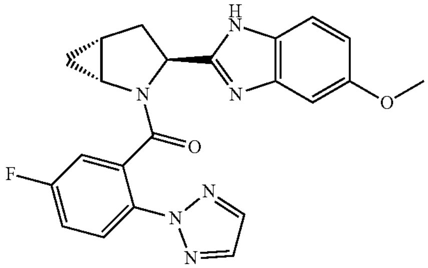

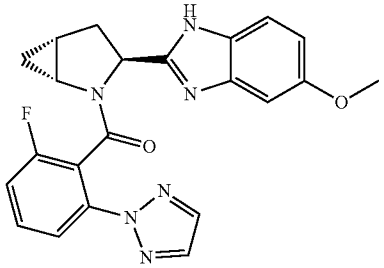

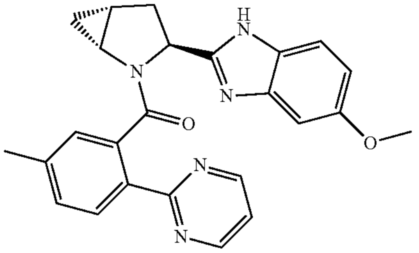

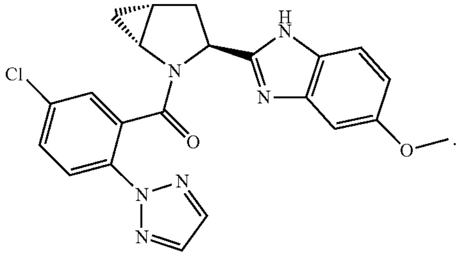

The present disclosure further provides an application of the compound or the pharmaceutically acceptable salt thereof described above in the manufacture of a medicament for treating a disease related to a selective orexin-2 receptor antagonist.

In some embodiments of the present disclosure, the disease related to a selective orexin-2 receptor antagonist is selected from insomnia and/or depression.

The present disclosure further provides following test method:

1. Determination of Pharmacokinetic Parameters in Rat Plasma 4 healthy SD rats aged 6-9 weeks were selected and randomly divided into two groups, with 2 rats in each group. One group was given the test compound at 2 mg/kg by intravenous injection, and the other group was given the test compound at 10 mg/kg by intragastric administration. Plasma samples were collected at 0.083, 0.25, 0.5, 1.0, 2.0, 4.0, 6.0, 8.0, and 24 h after administration for the intravenous injection group and intragastric administration group, respectively. Quantitative analysis of all biological samples was carried out by LC-MS/MS method, and the WinNonlin™ Version 6.3 (Pharsight, Mountain View, CA) pharmacokinetic software was used to calculate the relevant pharmacokinetic parameters by the non-compartmental model linear logarithmic trapezoidal method. $AUC_{0\text{-}last}$ represents area under the plasma concentration-time curve from time zero to the last detectable concentration time point; p.o. represents oral; i.v. represents intravenous injection; $T_{1/2}$ represents half-life; CL represents clearance rate; Vd represents apparent volume of distribution; $C_{max}$ represents peak concentration; $T_{max}$ represents time to peak; F % represents oral bioavailability.

2. Determination of Drug Concentration in Rat Brain Tissue 4 healthy SD rats aged 6-9 weeks were selected, and the other group was given the test compound at 10 mg/kg by intragastric administration. 2 animals were randomly selected at 0.5 h and 2 h after administration, respectively. Plasma and brain tissue samples were collected, and LC-MS/MS method was used for quantitative analysis of all biological samples.

Technical Effects

As an OX-2 receptor antagonist, the compound of the present disclosure has a selective antagonistic effect on the OX-2 receptor, exhibits good activity in in vitro tests, and can be used to develop a drug for the treatment of a mental disease related to Orexin signaling pathways such as insomnia and depression. The compound of the present disclosure exhibits good pharmacokinetic properties in rats, can penetrate the blood-brain barrier into the brain tissue in rats, and reach a high drug concentration.

Definition and Description

Unless otherwise stated, the following terms and phrases used herein are intended to have the following meanings. A specific term or phrase should not be considered uncertain or unclear unless specifically defined, but should be understood in its ordinary meaning. When a trade name appears herein, it is intended to refer to the corresponding commodity or an active ingredient thereof.

The term "pharmaceutically acceptable" as used herein refers to those compounds, materials, compositions and/or dosage forms, which are, within the scope of sound medical judgment, suitable for use in contact with human and animal tissues, without excessive toxicity, irritation, allergic reactions or other problems or complications, which is commensurate with a reasonable benefit/risk ratio.

The term "pharmaceutically acceptable salt" refers to a salt of the compound of the present disclosure, which is prepared from the compound having specific substituents found in the present disclosure with relatively non-toxic acids or bases. When compounds of the present disclosure contain relatively acidic functional groups, base addition salts can be obtained by contacting such compounds with a sufficient amount of base, either in pure solution or a suitable inert solvent. Pharmaceutically acceptable base addition salts include sodium, potassium, calcium, ammonium, organic amine or magnesium salts or similar salts. When compounds of the present disclosure contain relatively basic functional groups, acid addition salts can be obtained by contacting such compounds with a sufficient amount of acid, either in pure solution or a suitable inert solvent. Examples of pharmaceutically acceptable acid addition salts include salts of inorganic acids, which include, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid and phosphorous acid; and salts of organic acids, which include, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid; and also include salts of amino acids (such as arginine), and salts of organic acids such as glucuronic acid. Certain specific compounds of the present disclosure contain basic and acidic functional groups and thus can be converted to any base or acid addition salt.

The pharmaceutically acceptable salts of the present disclosure can be synthesized from a parent compound containing acid radicals or base radicals by conventional chemical methods. In general, the method for preparing such salts comprises: in water or an organic solvent or a mixture of both, reacting these compounds in free acid or base forms with a stoichiometric amount of a suitable base or acid to prepare the salts.

Unless otherwise specified, the term "$C_{1-3}$ alkyl" is used to represent a linear or branched saturated hydrocarbon group consisting of 1 to 3 carbon atoms. The $C_{1-3}$ alkyl includes $C_{1-2}$ alkyl, $C_{2-3}$ alkyl, etc.; and it can be monovalent (such as methyl), divalent (such as methylene) or multivalent (such as methine). Examples of $C_{1-3}$ alkyl include, but are not limited to, methyl (Me), ethyl (Et), propyl (including n-propyl and isopropyl), etc.

Unless otherwise specified, the term "$C_{1-3}$ alkoxy" means those alkyl groups comprising 1 to 3 carbon atoms that are connected to the rest of the molecule through one oxygen atom. The $C_{1-3}$ alkoxy includes $C_{1-2}$ alkoxy, $C_{2-3}$ alkoxy, $C_3$ alkoxy, $C_2$ alkoxy, etc. Examples of $C_{1-3}$ alkoxy include but are not limited to methoxy, ethoxy, propoxy (including n-propoxy and isopropoxy), etc.

Unless otherwise specified, "$C_{3-6}$ cycloalkyl" means a saturated cyclic hydrocarbon group consisting of 3 to 6 carbon atoms, which comprises a monocyclic and bicyclic ring system, and the $C_{3-6}$ cycloalkyl includes $C_{3-5}$, $C_{4-5}$, and $C_{5-6}$ cycloalkyl; and it can be monovalent, bivalent or multivalent. Examples of $C_{3-6}$ cycloalkyl include, but are not limited to, cyclopropyl, cyclobutyl, cyclopentyl, cyclohexyl, etc.

Unless otherwise specified, the term "halo" or "halogen" by itself or as part of another substituent means a fluorine, chlorine, bromine or iodine atom.

Unless otherwise stated, the term "isomer" is intended to include geometric isomers, cis-trans isomers, stereoisomers, enantiomers, optical isomers, diastereomers and tautomers.

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereomers, (D)-isomers, (L)-isomers, and racemic mixtures and other mixtures thereof, such as enantiomerically or diastereomerically enriched mixtures, all of which fall within the scope of the present disclosure. Additional asymmetric carbon atoms may be present in a substituent such as an alkyl group. All these isomers and mixtures thereof are included in the scope of the present disclosure.

Unless otherwise stated, the term “enantiomer” or “optical isomer” refers to stereoisomers that are mirror images of each other.

Unless otherwise stated, the term “cis-trans isomer” or “geometric isomer” is caused by the fact that double bonds or single bonds of ring-forming carbon atoms cannot rotate freely.

Unless otherwise stated, the term “diastereomer” refers to stereoisomers in which molecules have two or more chiral centers and are not mirror images of each other.

Unless otherwise stated, “(+)” represents right-handed, “(−)” represents left-handed, and “(±)” means racemic.

Unless otherwise stated, the wedge-shaped solid bond ( ) and the wedge-shaped dotted bond ( ) represent the absolute configuration of a stereoscopic center; the straight solid bond ( ) and the straight dotted bond ( ) represent the relative configuration of a stereoscopic center; the wavy line ( ) represents the wedge-shaped solid bond ( ) or the wedge-shaped dotted bond ( ); or the wavy line ( ) represents the straight solid bond ( ) or the straight dotted bond ( ).

Unless otherwise stated, the term “rich in one isomer”, “isomer enriched”, “rich in one enantiomer” or “enantiomerically enriched” refers to the content of one of the isomers or enantiomers is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise stated, the term “isomer excess” or “enantiomeric excess” refers to the difference between the relative percentages of two isomers or two enantiomers. For example, if the content of one isomer or enantiomer is 90%, and the content of the other isomer or enantiomer is 10%, the isomer or enantiomeric excess (ee value) is 80%.

Optically active (R)- and (S)-isomers and D and L isomers can be prepared using chiral synthesis or chiral reagents or other conventional techniques. If a particular enantiomer of a compound of the present disclosure is desired, it can be prepared by asymmetric synthesis or derivatization with a chiral auxiliary, wherein the resulting diastereomeric mixture is separated and the auxiliary groups are cleaved to provide pure desired enantiomers. Alternatively, where the molecule contains a basic functional group (such as an amino group) or an acidic functional group (such as a carboxyl group), diastereomeric salts can be formed with an appropriate optically active acid or base, followed by resolution of the diastereomers using conventional methods well known in the art, and subsequent recovery of the pure enantiomers. In addition, separation of enantiomers and diastereomers is frequently accomplished using chromatography, which uses chiral stationary phases, optionally in combination with chemical derivatization methods (e.g., formation of carbamates from amines).

The compounds of the present disclosure may contain unnatural proportions of atomic isotopes at one or more of the atoms constituting the compound. For example, the compounds may be radiolabeled with radioactive isotopes, such as tritium ($^3H$), iodine-125 ($^{125}I$) or C-14 ($^{14}C$). For another example, the hydrogen can be substituted by heavy hydrogen to form deuterated drugs. The bond formed by deuterium and carbon is stronger than the bond formed by ordinary hydrogen and carbon. Compared with undeuterated drugs, deuterated drugs have reduced toxic side effects, increased drug stability, enhanced efficacy, prolonged biological half-life of drugs and other advantages. All isotopic variations of the compounds of the present disclosure, whether radioactive or not, are intended to be encompassed within the scope of the present disclosure.

The term “optional” or “optionally” means that the subsequently described event or circumstance may, but not necessarily occur, and that the description includes instances where said event or circumstance occurs and instances where said event or circumstance does not occur.

The term “substituted” means that any one or more hydrogen atoms on the designated atom are substituted by a substituent, which may include heavy hydrogen and hydrogen variants, provided that the valence state of the designated atom is normal, and the substituted compound is stable. Where the substituent is oxygen (i.e., =O), it means that two hydrogen atoms are substituted. Oxygen substitution does not occur on aromatic groups.

The term “optionally substituted” means that it may or may not be substituted. Unless otherwise specified, the type and number of substituents may be arbitrary on the basis that they can be achieved in chemistry.

Where any variable (such as R) appears more than once in the composition or structure of a compound, its definition in each case is independent. Thus, for example, if a group is substituted with 0-2 R, the group can optionally be substituted with up to two R, and R in each case has independent options. In addition, combinations of substituents and/or variants thereof are permissible only if such combinations result in stable compounds.

When the number of a linking group is 0, such as $-(CRR)_0-$, it means that the linking group is a single bond.

When the number of a substituent is 0, it means that the substituent does not exist. For example, $-A-(R)_0$ means that the structure is actually -A.

When a substituent is vacant, it means that the substituent does not exist. For example, when X is vacant in A-X, it means that the structure is actually A.

When one of the variables is selected from a single bond, it means that the two groups to which it is connected are directly connected. For example, when L represents a single bond in A-L-Z, it means that the structure is actually A-Z.

When the bond of a substituent can be cross-connected to more than two atoms on a ring, the substituent can be bonded to any atom on the ring, for example, the structural unit

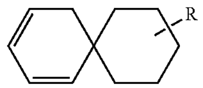 or 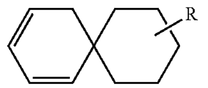

indicates that the substituent R can be substituted at any position on the cyclohexyl or cyclohexadiene. When the substituents listed do not indicate through which atom they are connected to the substituted group, such substituents can be bonded through any of the atoms thereof, for example, pyridyl as a substituent can be attached to the substituted group via any carbon atom on the pyridine ring.

When the linking group listed does not indicate the linking direction thereof, the linking direction is arbitrary, for example, the linking group L is -M-W— in

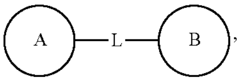

at this situation, -M-W— can connect ring A and ring B in the same direction as the reading order from left to right to form

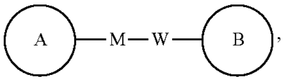

and can also connect ring A and ring B in the opposite direction as the reading order from left to right to form

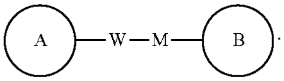

Combinations of the linking groups, substituents, and/or variants thereof are permissible only if such combinations result in stable compounds.

Unless otherwise specified, when a group has one or more connectable sites, any one or more sites of the group can be connected to other groups through chemical bonds. When the connection mode of the chemical bond is not positioned, and there is an H atom at the connectable site, the number of H atoms at the site will decrease correspondingly with the number of chemical bonds connected to become a group with the corresponding valence when the chemical bond is connected. The chemical bonds between the sites and other groups can be represented by a straight solid bond (), a straight dotted bond (), or a wavy line

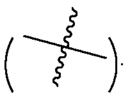

For example, the straight solid bond in —$OCH_3$ means that the group is connected to other groups through the oxygen atom in the group; the straight dotted bond in

means that the group is connected to other groups through the two ends of the nitrogen atom in the group; the wavy line in

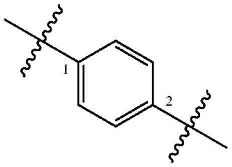 [SMILES: *c1ccc(*)cc1]

means that the group is connected to other groups through the 1 and 2 carbon atoms in the phenyl group;

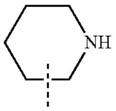

means that any connectable site on the piperidinyl can be connected to other groups through one chemical bond, including at least four connection modes:

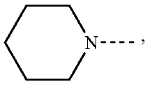 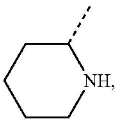 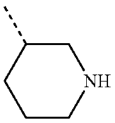 and 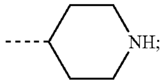

even if the H atom is drawn on —N—,

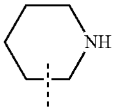

still includes the group of the connection mode

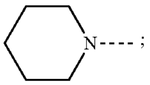

but the H at the site will decrease correspondingly by one and become the corresponding monovalent piperidinyl when one chemical bond is connected.

Unless otherwise specified, the number of atoms in a ring is usually defined as the member number of the ring. For example, "5- to 7-membered ring" means a "ring" with 5-7 atoms arranging in a circle.

The compounds of the present disclosure can be prepared by various synthetic methods well known to a person skilled in the art, including the specific embodiments listed below, the embodiments formed by the combination with other chemical synthesis methods, and equivalent alternative embodiments well known to a person skilled in the art, wherein the preferred embodiments include but are not limited to the examples of the present disclosure.

The structure of the compound of the present disclosure can be confirmed by conventional methods well known to a person skilled in the art. If the present disclosure relates to the absolute configuration of the compound, the absolute configuration can be confirmed by conventional technical means in the art. For example, single-crystal X-ray diffraction (SXRD) uses a Bruker D8 venture diffractometer to collect the diffraction intensity data of the cultivated single crystal, with a light source of CuKα radiation, and a scanning mode of (p/o scanning. After the related data is collected, a direct method (Shelxs97) is further used to resolve the crystal structure, so that the absolute configuration can be confirmed.

The present disclosure uses the following abbreviations: $H_2O$ represents water; eq represents equivalent; PE represents petroleum ether; EtOAc represents ethyl acetate; EtOH represents ethanol; MeOH represents methanol; HOAc represents acetic acid; HCl represents hydrochloric acid; HPLC represents high performance liquid chromatography; $H_2SO_4$ represents sulfuric acid; HCl/EtOAc represents a solution hydrochloric acid in ethyl acetate; HATU represents O-(7-azabenzotriazol-1-yl)-N,N,N',N'-tetramethylurea hexafluorophosphate; TFA represents trifluoroacetic acid; TEA represents triethylamine; DIEA or DIPEA represents N,N-diisopropylethylamine; mp represents melting point; ° C. represents celsius degree; h represents hour; mL represents milliliter; mM represents millimole per liter; mmol represents millimole; mol represents micromole; HNMR represents hydrogen nuclear magnetic resonance spectrum; MS represents mass spectrum; min represents minute; pH represents the negative logarithm of the hydrogen ion molar concentration; SFC represents supercritical liquid chromatography.

The solvents used in the present disclosure are commercially available.

Compounds are named by hand or using ChemDraw® software, and commercially available compounds are named by the supplier catalog names.

DETAILED DESCRIPTION OF THE PREFERRED EMBODIMENT

The present disclosure will be described in detail with the following examples, but not imply any adverse limitation to the present disclosure. The present disclosure has been described in detail herein, and the specific embodiments thereof are also disclosed therein. For a person skilled in the art, without departing from the spirit and scope of the present disclosure, all the variations and improvements made to the specific embodiments of the present disclosure would have been obvious.

Example 1

Compound 1

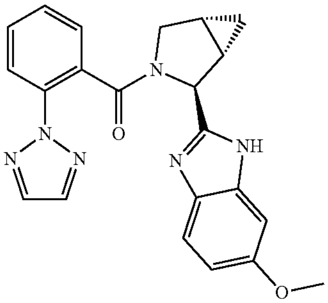

Synthetic Route:

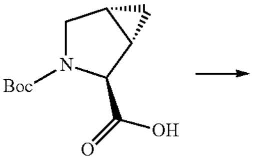

Compound 1-1

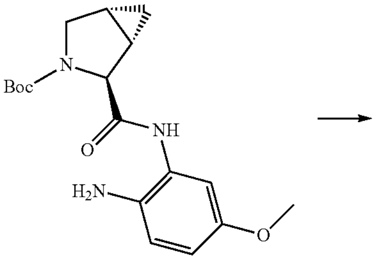

Compound 1-2

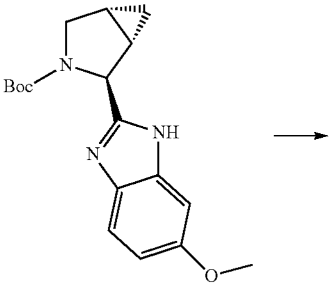

Compound 1-3

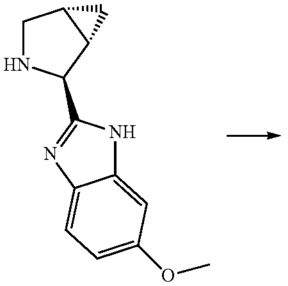

Compound 1-4

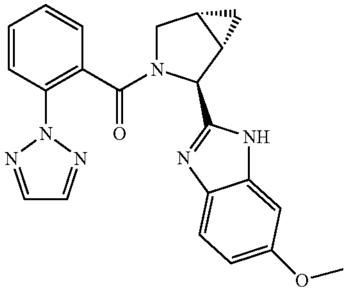

Compound 1

Step 1: Synthesis of Compound 1-2

Compound 1-1 (233 mg), 4-methoxy-o-phenylenediamine (169.99 mg), HATU (584.76 mg), DIPEA (267.88 μL) and solvent DMF (3 mL) were added to a pre-dried flask, and stirred for 15 h at 25° C. under nitrogen protection. After the reaction was completed, the reaction was quenched by adding water (40 mL), and extracted with ethyl acetate (20 mL×2), and the organic phases were combined, dried over anhydrous sodium sulfate, filtered, and concentrated under reduced pressure to obtain a crude product, which was purified by a flash silica gel column (petroleum ether:ethyl acetate=60:40) to obtain compound 1-2. $^1$H NMR (400 MHz, $CDCl_3$) δ ppm 6.93-7.20 (m, 1H), 6.31 (br d, J=12.30 Hz, 2H), 4.43 (s, 1H), 3.80-4.01 (m, 2H), 3.75 (s, 3H), 3.37-3.72 (m, 2H), 1.92 (br s, 1H), 1.62 (br s, 1H), 1.46 (s, 9H), 0.82 (br d, J=6.02 Hz, 1H), 0.23 (q, J=4.27 Hz, 1H).

Step 2: Synthesis of Compound 1-3

Compound 1-2 (100 mg) and glacial acetic acid (5 mL) were added to a pre-dried flask, and stirred at 100° C. for 5 h. After the reaction was complete, the reaction was quenched by adding water (20 mL), and extracted with ethyl acetate (20 mL) and saturated $NaHCO_3$ (30 mL×3), and the organic phases were combined, dried over anhydrous sodium sulfate, filtered, and concentrated under reduced pressure to obtain crude product compound 1-3, which was directly used in the next step without purification. LCMS m/z=330.0[M+H]$^+$ Step 3: Synthesis of the Trifluoroacetate of Compound 1-4

Compound 1-3 (90 mg) and solvent DCM (2 mL) were added to a pre-dried flask, then TFA (2 mL) was added, and stirred for 1 h at 25° C. under nitrogen protection. After the reaction was completed, the reaction liquid was concentrated to dryness to obtain the crude trifluoroacetate of compound 1-4, which was directly used in the next step without purification. LCMS m/z=230.0[M+H]$^+$ Step 4: Synthesis of Compound 1

The trifluoroacetate of compound 1-4 (60 mg), 2-(2H-1,2,3-triazol-2-yl)benzoic acid (64.36 mg), HATU (149.25 mg), DIPEA (68.37 μL) and solvent DMF (3 mL) were added to a pre-dried flask and stirred at 25° C. for 15 h. After the reaction was completed, the reaction liquid was diluted with ethyl acetate (10 mL) and extracted with water (20 mL×2). The organic phases were combined, dried over anhydrous sodium sulfate, filtered, and concentrated under reduced pressure to obtain a crude product, which was subjected to Pre-HPLC (column type: Phenomenex Gemini-NX 80*30 mm*3 μm; mobile phase: [$H_2O$ (10 mM $NH_4HCO_3$)-ACN]; ACN %: 30%-60%, 9 min) for separation to obtain compound 1. $^1$H NMR (400 MHz, DMSO-$d_6$) δ ppm 12.08 (br s, 1H), 8.24-8.00 (m, 1H), 7.99-7.70 (m, 2H), 7.68-7.25 (m, 4H), 7.21-6.99 (m, 1H), 6.94-6.72 (m, 1H), 5.35 (s, 0.63H), 4.65 (s, 0.37H), 3.97-3.60 (m, 5H), 1.95-1.52 (m, 2H), 0.91-0.43 (m, 2H). LCMS m/z=401.2 [M+H]$^+$

Example 2

Compound 2

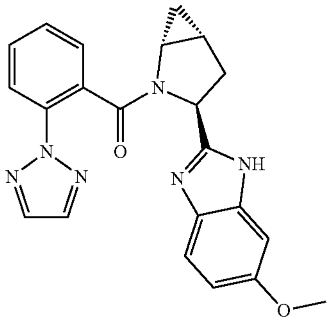

Synthetic Route:

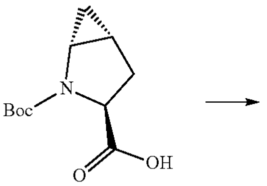

Compound 2-1

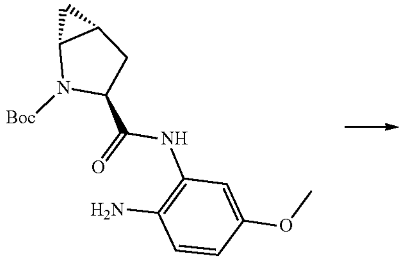

Compound 2-2

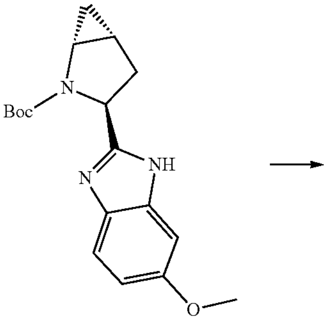

Compound 2-3

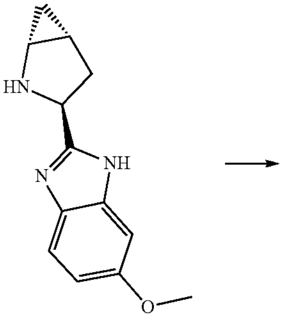

Compound 2-4

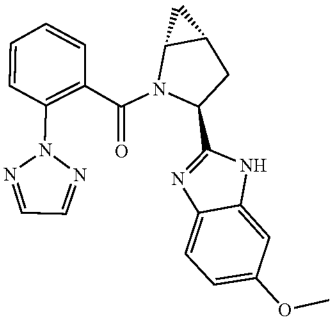

Compound 2

Step 1: Synthesis of Compound 2-2

Compound 2-1 (500 mg), HATU (1.25 g) and DMF (10 mL) were added to a pre-dried flask, then 4-methoxy-o- phenylenediamine (364.79 mg) and DIPEA (1.15 mL) were added and stirred at 15° C. for 15 h. After the reaction was completed, the reaction liquid was diluted with ethyl acetate (80 mL), washed with water (100 mL) and brine (100 mL×2). The organic phase was dried over anhydrous sodium sulfate, filtered, and concentrated under reduced pressure to obtain a crude product, which was purified by a flash silica gel column (petroleum ether:ethyl acetate=30:70) to obtain compound 2-2. $^1$H NMR (400 MHz, DMSO-$d_6$) δ 9.03 (br s, 1H), 6.73-7.06 (m, 1H), 6.04-6.34 (m, 2H), 4.68-5.01 (m, 2H), 3.96 (br s, 1H), 3.65 (s, 3H), 3.37 (br s, 1H), 2.22-2.39 (m, 1H), 2.06-2.20 (m, 1H), 1.59 (br s, 1H), 1.29-1.47 (m, 9H), 0.72 (td, J=5.55, 8.47 Hz, 1H), 0.42 (br s, 1H).

Step 2: Synthesis of Compound 2-3

Compound 2-2 (500 mg) and glacial acetic acid (10 mL) were added to a pre-dried flask, and stirred at 100° C. for 1.5 h. After completion of the reaction, the reaction liquid was directly concentrated under reduced pressure to obtain a crude product. Saturated sodium bicarbonate (80 mL) was added to the crude product and extracted with DCM/MeOH (80 mL×2, 10/1), and the organic phases were combined, dried over anhydrous sodium sulfate, filtered, and concentrated under reduced pressure to obtain a crude product. The crude product was purified with a flash silica gel column (petroleum ether:ethyl acetate=50:50) to obtain compound 2-3, $^1$H NMR (400 MHz, $CDCl_3$) δ 10.41 (br s, 1H), 6.85-7.74 (m, 3H), 4.99 (br s, 1H), 3.84 (s, 3H), 3.24 (br s, 2H), 2.40 (br t, J=10.92 Hz, 1H), 1.81 (br s, 1H), 1.50 (br s, 9H), 0.91 (td, J=5.62, 8.60 Hz, 1H), 0.50 (br s, 1H).

Step 3: Synthesis of the Hydrochloride of Compound 2-4

Compound 2-3 (300 mg) and solvent ethyl acetate (8 mL) were added to a pre-dried flask, then HCl/EtOAc (4 M, 8 mL) was added, and stirred at 15° C. for 15 h. After the reaction was completed, the reaction liquid was directly concentrated and spin-dried to obtain the hydrochloride of compound 2-4. $^1$H NMR (400 MHz, DMSO-$d_6$) δ 10.71 (br s, 1H), 7.64 (d, J=9.03 Hz, 1H), 7.19 (d, J=2.26 Hz, 1H), 7.03 (dd, J=2.38, 8.91 Hz, 1H), 4.79-4.93 (m, 1H), 3.83 (s, 3H), 3.37-3.49 (m, 1H), 2.53-2.67 (m, 2H), 1.95 (br dd, J=4.27, 8.53 Hz, 1H), 1.09-1.20 (m, 1H), 0.80-0.92 (m, 1H).

Step 4: Synthesis of Compound 2

2-(2H-1,2,3-triazol-2-yl)benzoic acid (128.14 mg), HATU (372.02 mg) and dichloromethane (10 mL) were added to a pre-dried flask, and then the hydrochloride of compound 2-4 (200 mg) and DIEA (393.27 μL) were added, and stirred for 15 h at 15° C. After the reaction was complete, the reaction liquid was diluted with dichloromethane (80 mL), and washed with water (80 mL) and brine (80 mL×2). The organic phase was dried over anhydrous sodium sulfate, filtered, and concentrated under reduced pressure to obtain a crude product. The crude product was purified by a flash silica gel column (petroleum ether:ethyl acetate=30:70) to obtain compound 2. $^1$H NMR (400 MHz, $CDCl_3$) δ 8.06 (d, J=8.28 Hz, 1H), 7.53-7.64 (m, 4H), 7.44-7.51 (m, 2H), 7.05 (d, J=2.01 Hz, 1H), 6.94 (dd, J=2.26, 9.03 Hz, 1H), 5.58 (br d, J=5.77 Hz, 1H), 3.81 (s, 3H), 2.97-3.09 (m, 2H), 2.44 (dd, J=9.66, 13.18 Hz, 1H), 1.89-2.00 (m, 1H), 0.73 (br s, 1H), 0.53 (br s, 1H). LCMS m/z=401.1[M+H]$^+$.

Example 3

Compound 3

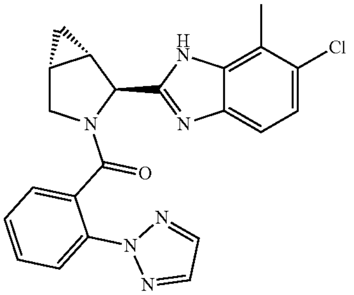

Synthetic Route:

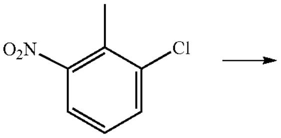

Compound 3-1

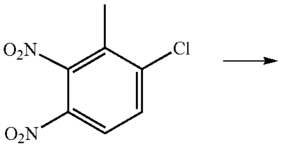

Compound 3-2

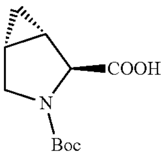

Compound 1-1

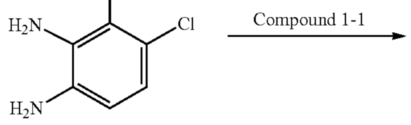

Compound 3-3

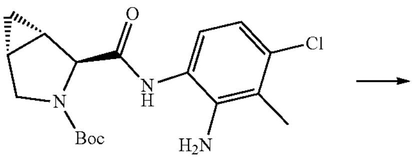

Compound 3-4

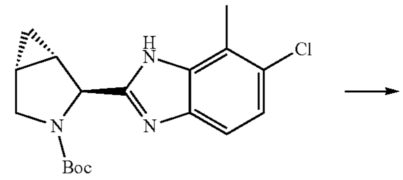

Compound 3-5

-continued

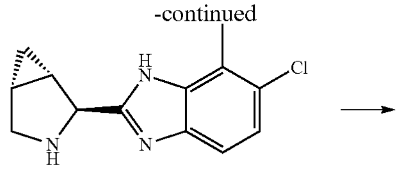

Compound 3-6

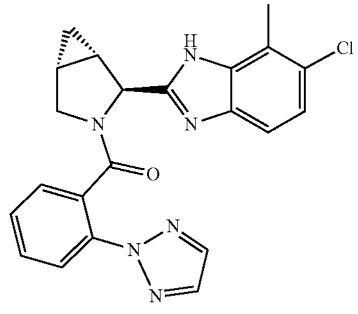

Compound 3

Step 1: Synthesis of Compound 3-2

$H_2SO_4$ (50.00 mL) was added to a dry vial, then $HNO_3$ (2.84 mL, 65% concentration) was slowly added dropwise at 0° C., and then compound 3-1 (5 g) was added slowly, and the reaction was stirred at 15° C. for 16 h. The reaction liquid was slowly poured into 100 mL of ice water, then the aqueous phase was extracted with methyl tert-butyl ether (20 mL×2), and the organic phases were combined, dried over anhydrous sodium sulfate, filtered and concentrated. The crude product was homogenized with 50 mL of petroleum ether for 1 h and then filtered. The filter cake was collected, concentrated and dried to obtain compound 3-2. $^1H$ NMR (400 MHz, $CDCl_3$) δ: 8.06 (d, J=8.8 Hz, 1H), 7.70 (d, J=8.8 Hz, 1H), 2.43 (s, 3H). MS m/z: 239[M+23]$^+$.

Step 2: Synthesis of Compound 3-3

Compound 3-2 (4.6 g) was dissolved in EtOH (100 mL) and $H_2O$ (50 mL) in a one-necked flask, Fe powder (11.86 g) and $NH_4Cl$ (22.72 g) were added, and the reaction was stirred at 75° C. for 16 h. The reaction liquid was diluted by adding 200 mL of ethanol and then filtered, the filter cake was washed with ethanol (200 mL×2). The filtrate was concentrated, and then dissolved by adding 500 mL of ethyl acetate, homogenated for 30 minutes and filtered, and the filtrate was concentrated. The crude product was separated and purified by column chromatography (PE:EtOAc=10:1 to 1:1) to obtain compound 3-3. $^1H$ NMR (400 MHz, $CDCl_3$) δ: 6.74 (d, J=8.4 Hz, 1H), 6.55 (d, J=8.4 Hz, 1H), 3.41 (br s, 4H), 2.26 (s, 3H). MS m/z: 157[M+H]$^+$.

Step 3: Synthesis of Compound 3-4

Compound 3-3 (227.42 mg) and compound 1-1 (300 mg) were dissolved in DMF (10 mL) in a dry vial, and DIEA (511.83 mg) and a solution of tri-n-propylcyclophosphoric anhydride in ethyl acetate (785.10 μL, 50% content) were added under nitrogen protection at 0° C., and then the reaction was stirred at 15° C. for 16 h. The reaction liquid was poured into 50 mL of water, the aqueous phase was extracted with ethyl acetate (20 mL×3), the organic phases were combined and washed with water (20 mL×2), dried over anhydrous sodium sulfate, filtered and concentrated. The crude product was separated and purified by column chromatography (PE:EtOAc=10:1 to 1:1) to obtain compound 3-4. MS m/z: 310[M+H−56]$^+$.

Step 4: Synthesis of Compound 3-5

Compound 3-4 (450 mg) was dissolved in DMF (8 mL) in a dry vial and AcOH (703.44 μL) was added, and the reaction was stirred at 130° C. for 2 h. The reaction liquid was poured into 50 mL of water, the aqueous phase was extracted with ethyl acetate (20 mL×3), the organic phases were combined and washed with water (20 mL×2), dried over anhydrous sodium sulfate, filtered and concentrated. The crude product was separated and purified by column chromatography (PE:EtOAc=10:1 to 1:1) to obtain compound 3-5, MS m/z 348[M+H]$^+$.

Step 5: Synthesis of the Hydrochloride of Compound 3-6

Compound 3-5 (310 mg) was dissolved in EtOAc (5 mL) in a dry vial and HCl/EtOAc (4 M, 4.46 mL) was added and the reaction was stirred at 15° C. for 16 h. The reaction liquid was concentrated under reduced pressure to obtain the crude product—the hydrochloride of compound 3-6, which was directly used in the next step without further purification, MS m/z: 248[M+H]+.

Step 6: Synthesis of Compound 3

The hydrochloride of compound 3-6 (100 mg) and 2-(2H-1,2,3-triazol-2-yl) benzoic acid (66.57 mg) were dissolved in THE (5 mL) in a dry vial, and TEA (146.93 μL) and a solution of tri-n-propylcyclophosphoric anhydride in ethyl acetate (418.55 μL, 50% purity) were added, and the reaction was further stirred at 50° C. for 16 h under nitrogen protection. After the reaction was completed, the reaction liquid was poured into 20 mL of water, the aqueous phase was extracted with ethyl acetate (10 mL×2), and the organic phases were combined, dried with anhydrous sodium sulfate, filtered and concentrated. The crude product was separated and purified by preparative HPLC (chromatographic column: Phenomenex Gemini-NX 80*40 mm*3 μm; mobile phase: [water (containing 10 mM $NH_4HCO_3$)-acetonitrile]; acetonitrile %: 35%-65%, 8 min) to obtain compound 3. $^1H$ NMR (400 MHz, DMSO-d$^6$) δ: 8.30-7.89 (m, 3H), 7.66-7.63 (m, 1H), 7.58-7.31 (m, 3H), 7.24-7.20 (m, 1H), 5.39 (s, 1H), 4.15-3.86 (m, 1H), 2.67-2.59 (m, 3H), 2.43-2.32 (m, 1H), 1.82-1.58 (m, 3H), 0.80-0.52 (m, 3H). MS m/z: 419 [M+H]$^+$.

Example 4

Compound 4

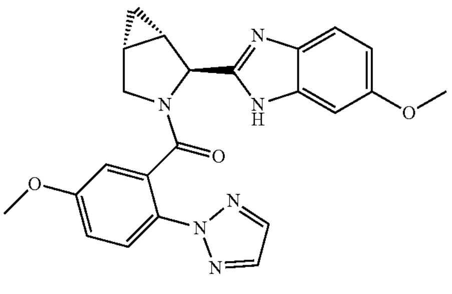

Synthetic Route:

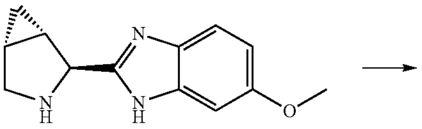

Compound 1-4

-continued

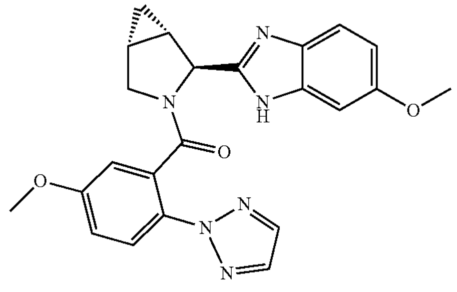

Compound 4

Step 1: Synthesis of Compound 4

The trifluoroacetate of compound 1-4 (100 mg) and 5-methoxy-2-(2H-1,2,3-triazol-2-yl)benzoic acid (82.49 mg) were dissolved in THE (5 mL) in a dry vial, and TEA (157.13 μL) and a solution of tri-n-propylcyclophosphoric anhydride in ethyl acetate (447.61 μL, 50% content) were added, and the reaction was stirred at 50° C. for 16 h under nitrogen protection. The reaction liquid was poured into 20 mL of water, the aqueous phase was extracted with ethyl acetate (10 mL×2), and the organic phases were combined, dried with anhydrous sodium sulfate, filtered and concentrated. The crude product was separated and purified by preparative HPLC (chromatographic column: Phenomenex Gemini-NX 80*40 mm*3 μm; mobile phase: [water (10 mM $NH_4HCO_3$)-acetonitrile]; acetonitrile %: 25%-55%, 8 min) to obtain compound 4. $^1H$ NMR (400 MHz, DMSO-$d_6$) δ: 12.17-12.10 (m, 1H), 8.09-8.08 (m, 2H), 7.77-7.70 (m, 1H), 7.49-7.47 (m, 1H), 7.41-7.32 (m, 1H), 7.20-7.00 (m, 2H), 6.93-6.79 (m, 1H), 5.31-4.74 (m, 1H), 3.99-3.76 (m, 6H), 3.07 (m, 1H), 2.51-2.49 (m, 1H), 1.66-1.63 (m, 2H), 0.77-0.54 (m, 2H). MS m/z: 431[M+H]$^+$.

Example 5

Compound 5

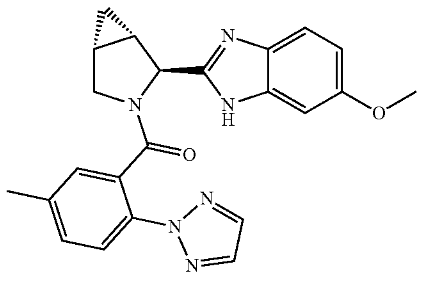

Synthetic Route:

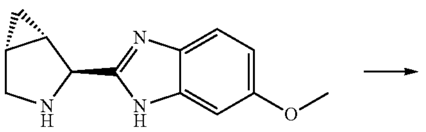

Compound 1-4

-continued

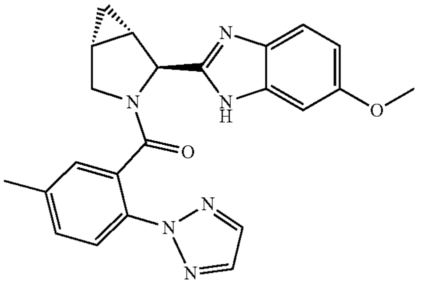

Compound 5

The trifluoroacetate of compound 1-4 (50 mg), 5-methyl-2-(2H-1,2,3-triazol-2-yl)benzoic acid (44.31 mg) and THF (1 mL) were added to a reaction flask, and TEA (151.77 μL) and a solution of tri-n-propylcyclophosphoric anhydride in ethyl acetate (194.54 μL, 50% content) were added under stirring and reacted at 50° C. for 16 h. Water (10 mL) was added to the reaction liquid, extracted with ethyl acetate (3×10 mL), and the organic phases were combined, dried over anhydrous sodium sulfate, and concentrated under reduced pressure to obtain a crude product, which is purified by preparative HPLC (column: Phenomenex Gemini-NX C18 75*30 mm*3 m; mobile phase: [water (10 mM $NH_4HCO_3$)-acetonitrile]; acetonitrile %: 25%-45%, 8 min), to obtain compound 5. $^1H$ NMR (400 MHz, DMSO-$d_6$) δ: 10.97-12.91 (m, 1H), 7.81-8.39 (m, 1H), 7.67-7.80 (m, 1H), 7.22-7.65 (m, 3H), 6.87-7.21 (m, 1H), 6.72-6.86 (m, 1H), 6.15-6.58 (m, 1H), 4.61-5.38 (m, 1H), 3.82-4.02 (m, 1H), 3.75-3.81 (m, 3H), 2.56 (br s, 1H), 2.38-2.44 (m, 2H), 1.57-1.86 (m, 3H), 0.72-0.80 (m, 1H), 0.51-0.61 (m, 1H). MS m/z: 415 [M+H]$^+$.

Example 6

Compound 6

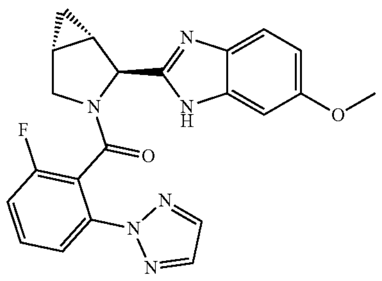

Synthetic Route:

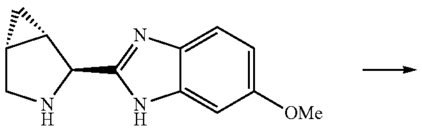

Compound 1-4

-continued

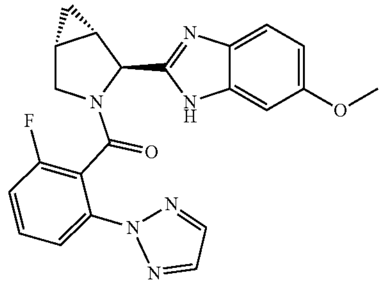

Compound 6

The trifluoroacetate of compound 1-4 (100 mg), 2-fluoro-6-(2H-1,2,3-triazol-2-yl)benzoic acid (99.39 mg) and THE (2 mL) were added to a reaction flask and stirred, and TEA (303.54 μL) and a solution of tri-n-propylcyclophosphoric anhydride in ethyl acetate (389.09 μL, 50% content) were added and reacted at 50° C. for 16 h. Water (10 mL) was added to the reaction liquid, extracted with ethyl acetate (3×10 mL), and the organic phases were combined, dried over anhydrous sodium sulfate, and concentrated under reduced pressure to obtain a crude product, which is separated and purified by preparative HPLC (column: Phenomenex Gemini-NX C18 75*30 mm*3 m; mobile phase: [water (10 mM $NH_4HCO_3$)-acetonitrile]; acetonitrile %: 25%-45%, 8 min), to obtain compound 6. $^1$H NMR (400 MHz, DMSO-$d_6$) δ: 11.53-12.33 (m, 1H), 8.15-8.26 (m, 1H), 7.74-7.90 (m, 1H), 7.60-7.73 (m, 1H), 7.11-7.60 (m, 3H), 6.52-7.10 (m, 2H), 4.52-5.50 (m, 1H), 3.90-4.22 (m, 1H), 3.79 (d, J=13.13 Hz, 3H), 3.21-3.50 (m, 1H), 1.53-1.94 (m, 2H), 0.33-0.88 (m, 2H). MS m/z: 419 $[M+H]^+$.

Example 7

Compound 7

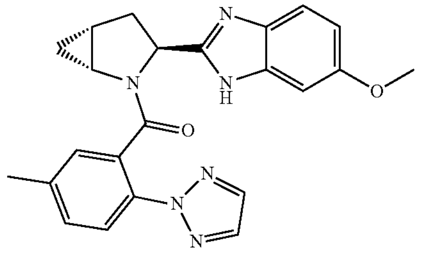

Synthetic Route:

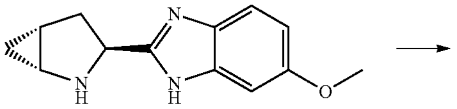

Compound 2-4

-continued

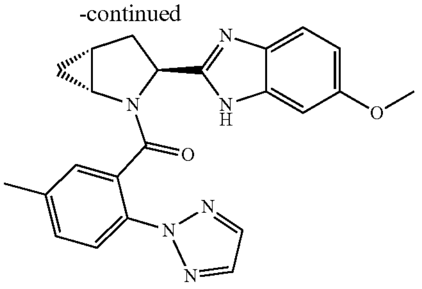

Compound 7

The hydrochloride of compound 2-4 (100 mg), 5-methyl-2-(2H-1,2,3-triazol-2-yl)benzoic acid (97.49 mg) and THE (2 mL) were added to a reaction flask and stirred, and TEA (607.08 μL) and a solution of tri-n-propylcyclophosphoric anhydride in ethyl acetate (778.18 μL, 50% content) were added and reacted at 15° C. for 16 h. After the reaction was completed, water (10 mL) was added, and extracted with ethyl acetate (3×10 mL), and the organic phases were combined, dried over anhydrous sodium sulfate, and concentrated under reduced pressure to obtain a crude product. The crude product was purified by preparative HPLC (column: Waters Xbridge BEH C18 100*30 mm*10 m; mobile phase: [water (10 mM $NH_4HCO_3$)-acetonitrile]; acetonitrile %: 20%-50%, 8 min) to obtain compound 7. $^1$H NMR (400 MHz, DMSO-$d_6$) δ: 11.75-12.09 (m, 1H), 7.87-8.16 (m, 2H), 7.63-7.85 (m, 1H), 7.41-7.53 (m, 2H), 6.38-7.40 (m, 3H), 4.60-5.20 (m, 1H), 3.73-3.79 (m, 3H), 3.11 (br d, J=6.02 Hz, 1H), 2.30-2.45 (m, 4H), 1.52-1.81 (m, 2H), 0.46-0.98 (m, 2H). MS m/z: 415 $[M+H]^+$.

Chiral purity was detected by chiral SFC (column: Chiralcel OD-3, 50×4.6 mm I.D., 3 m; mobile phase: [supercritical $CO_2$-methanol (containing 0.1% isopropylamine)]; methanol (containing 0.1% isopropylamine) %: 5%-50%, 3 min), retention time=1.161 min, ee=100%.

Example 8

Compound 8

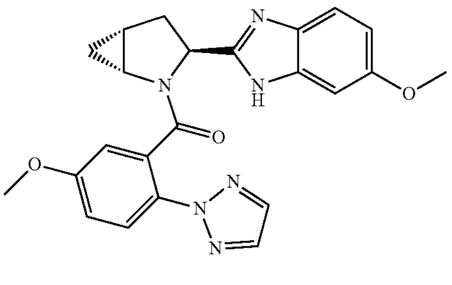

Synthetic Route:

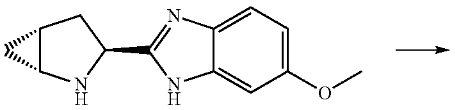

Compound 2-4

-continued

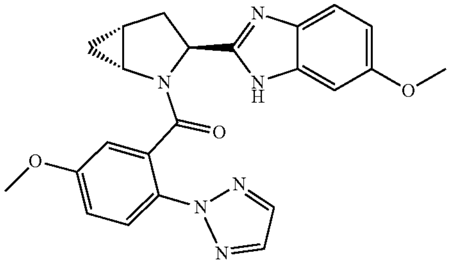

Compound 8

The hydrochloride of compound 2-4 (100 mg), 5-methoxy-2-(2H-1,2,3-triazol-2-yl)benzoic acid (105.16 mg) and THE (2 mL) were added to a reaction flask and stirred, and TEA (607.08 μL) and a solution of tri-n-propylcyclophosphoric anhydride in ethyl acetate (778.18 μL, 50% content) were added and reacted at 15° C. for 16 h. After the reaction was completed, water (10 mL) was added, and extracted with ethyl acetate (3x10 mL), and the organic phases were combined, dried over anhydrous sodium sulfate, and concentrated under reduced pressure to obtain a crude product. The crude product was purified by preparative HPLC (column: Waters Xbridge BEH C18 100*30 mm*10 m; mobile phase: [water (10 mM $NH_4HCO_3$)-acetonitrile]; acetonitrile %: 20%-95%, 8 min) to obtain compound 8. $^1H$ NMR (400 MHz, DMSO-$d_6$) δ: 11.71 (s, 1H), 7.99-8.15 (m, 1H), 7.81-7.91 (m, 2H), 7.38-7.72 (m, 1H), 7.07-7.36 (m, 2H), 6.44-7.03 (m, 2H), 4.76-5.18 (m, 1H), 3.63-3.91 (m, 6H), 3.17-3.20 (m, 1H), 2.34-2.38 (m, 1H), 1.70-1.85 (m, 1H), 1.11 (s, 1H), 0.55-0.89 (m, 2H). MS m/z: 431 $[M+H]^+$. Optical rotation value: (+) 60.99°+0.13° (10.38 mg/mL chloroform solution, length=50 mm, temperature=20° C., n=2). Chiral purity was detected by chiral SFC (column: Chiralpak AS-3, 50x4.6 mm I.D., 3 m; mobile phase: [supercritical $CO_2$-methanol (containing 0.1% isopropylamine)]; methanol (containing 0.1% isopropylamine) %: 5%-50%, 3 min), retention time=0.980 min, ee=100%.

Example 9

Compound 9

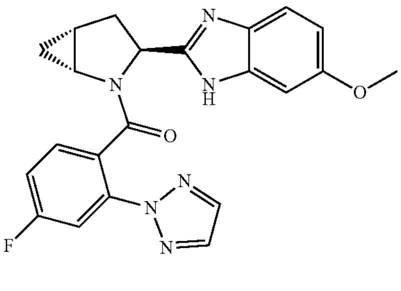

Synthetic Route:

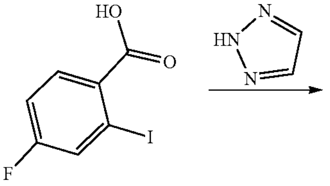

Compound 9-1

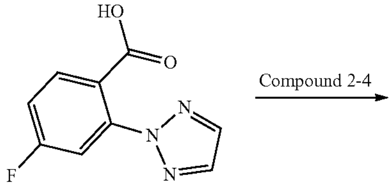

Compound 9-2

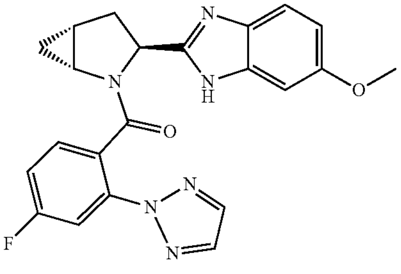

Compound 9

Step 1: Synthesis of Compound 9-2

Compound 9-1 (4.5 g), 1H-1,2,3-triazole (1.29 g), 1,10-phenanthroline (152.43 mg), cesium carbonate (8.27 g) and 1,4-dioxane (45 mL) were added to a reaction flask, and cuprous iodide (322.18 mg) was added, nitrogen replacement was performed three times and the reaction was performed at 100° C. for 16 h. After the reaction was complete, water was added to the reaction liquid (10 mL), pH was adjusted to 1-2 with HCl, and ethyl acetate (3x50 mL) was used for extraction. The organic phases were combined, dried over anhydrous sodium sulfate, and concentrated under reduced pressure to obtain a crude product. The crude product was separated and purified by silica gel column chromatography (eluent: DCM:MeOH=100:1 to 50:1) to obtain compound 9-2. $^1H$ NMR (400 MHz, DMSO-$d_6$) δ: 13.1 (s, 1H), 7.85 (s, 2H), 7.81-7.83 (m, 1H), 7.65-7.68 (m, 1H), 7.46-7.65 (m, 1H). MS m/z: 208 $[M+H]^+$.

Step 2: Synthesis of Compound 9

Compound 9-2 (100.00 mg) and toluene (1 mL) were added to a reaction flask and stirred, and thionyl chloride (38.52 μL) was added and reacted at 50° C. for 1 h, the reaction liquid was concentrated under reduced pressure, and dissolved in 0.5 mL of dichloromethane for later use. The hydrochloride of compound 2-4 (100 mg), dichloromethane (1 mL), and triethylamine (261.89 μL) were added to a reaction flask, stirred and cooled down to 0° C. The above dichloromethane solution was added dropwise and reacted at 15° C. for 16 h. After the reaction was complete, water was added to the reaction liquid (10 mL), and ethyl acetate (3x10 mL) was used for extraction. The organic phases were combined, dried over anhydrous sodium sulfate, and concentrated under reduced pressure to obtain a crude product. The crude product was purified by preparative HPLC (column: Waters Xbridge BEH C18 100*30 mm*10 m; mobile phase: [water (10 mM $NH_4HCO_3$)-acetonitrile]; acetonitrile %: 25%-55%, 8 min) to obtain compound 9. $^1H$ NMR (400 MHz, $CDCl_3$) δ: 9.59-11.75 (m, 1H), 7.82 (d, J=2.4, 1H), 7.35-7.69 (m, 4H), 7.04-7.23 (m, 2H), 6.95 (d, J=4, 1H), 5.63 (m, 1H), 3.88 (s, 3H), 3.53 (m, 1H), 2.72-2.83 (m, 1H), 2.30 (m, 1H), 1.92-2.08 (m, 1H), 0.74-0.91 (m, 1H), 0.36-0.62 (m, 1H). MS m/z: 419 $[M+H]^+$.

Example 10

Compound 10

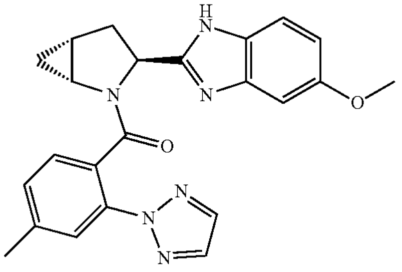

Synthetic Route:

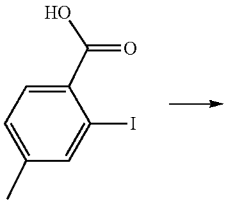

Compound 10-1

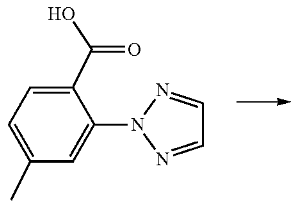

Compound 10-2

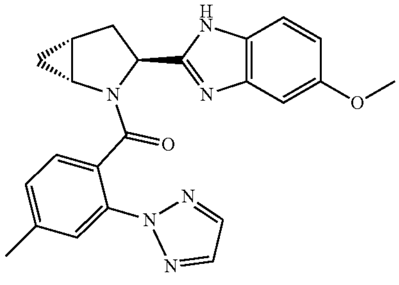

Compound 10

Step 1: Synthesis of Compound 10-2

Compound 10-1 (2.8 g), 1H-1,2,3-triazole (811.78 mg), cesium carbonate (5.22 g), 1,10-phenanthroline (96.28 mg) and 1,4-dioxane (28 mL) were added to a reaction flask, and cuprous iodide (203.50 mg) was added and reacted at 100° C. for 16 h. After the reaction was complete, water was added to the reaction liquid (10 mL), pH was adjusted to 1-2 with HCl, and ethyl acetate (3×50 mL) was used for extraction. The organic phases were combined, dried over anhydrous sodium sulfate, and concentrated under reduced pressure to obtain a crude product. The crude product was separated and purified by silica gel column chromatography (eluent: DCM:MeOH=100:1 to 50:1) to obtain compound 10-2. $^1H$ NMR (400 MHz, DMSO-$d_6$) δ: 12.9 (s, 1H), 8.06 (s, 2H), 7.67 (d, J=8, 1H), 7.55 (s, 1H), 7.39 (d, J=6.8, 1H), 2.43 (s, 3H). MS m/z: 204 $[M+H]^+$.

Step 2: Synthesis of Compound 10

The hydrochloride of compound 2-4 (100 mg), compound 10-2 (97.49 mg) and tetrahydrofuran (2 mL) were added to a reaction flask and stirred, and triethylamine (607.08 μL) and a solution of tri-n-propylcyclophosphoric anhydride in ethyl acetate (778.18 μL, 50% content) were added and reacted at 15° C. for 16 h. After the reaction was complete, water was added to the reaction liquid (10 mL), and ethyl acetate (3×10 mL) was used for extraction. The organic phases were combined, dried over anhydrous sodium sulfate, and concentrated under reduced pressure to obtain a crude product. The crude product was purified by preparative HPLC (column: Waters Xbridge BEH C18 100*30 mm*10 m; mobile phase: [water (containing 10 mM $NH_4HCO_3$)-acetonitrile]; acetonitrile %: 25%-45%, 8 min)-acetonitrile]; acetonitrile %: 45%-75%, 10 min) to obtain compound 10. $^1H$ NMR (400 MHz, DMSO-$d_6$) δ: 11.72-12.20 (m, 1H), 7.87-8.19 (m, 2H), 7.76 (s, 1H), 7.56-7.66 (m, 1H), 6.71-7.47 (m, 4H), 4.53-5.32 (m, 1H), 3.62-3.81 (m, 3H), 3.30 (s, 1H), 3.02-3.14 (m, 1H), 2.44 (s, 3H), 2.21-2.31 (m, 1H), 1.66-1.80 (m, 1H), 0.49-1.04 (m, 2H). MS m/z: 415 $[M+H]^+$.

Example 11

Compound 11

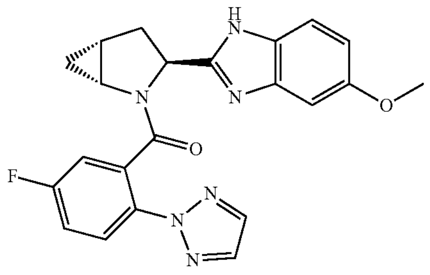

Synthetic Route:

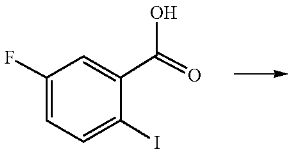

Compound 11-1

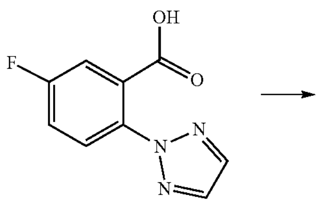

Compound 11-2

-continued

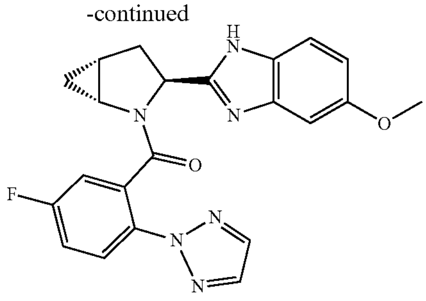

Compound 11

Step 1: Synthesis of Compound 11-2

Compound 11-1 (3 g), 1H-1,2,3-triazole (856.80 mg), cesium carbonate (5.51 g), 1,10-phenanthroline (101.62 mg) and 1,4-dioxane (30 mL) were added to a reaction flask, and cuprous iodide (214.79 mg) was added and reacted at 100° C. for 16 h. After the reaction was complete, water was added to the reaction liquid (10 mL), pH was adjusted to 1-2 with HCl, and ethyl acetate (3×50 mL) was used for extraction. The organic phases were combined, dried over anhydrous sodium sulfate, and concentrated under reduced pressure to obtain a crude product. The crude product was separated and purified by silica gel column chromatography (eluent: DCM:MeOH=100:1 to 50:1) and the obtained product was purified by preparative HPLC (chromatographic column: Phenomenex luna C18 (250*70 mm, 15 m); mobile phase: [water (containing HCl)-acetonitrile]; acetonitrile %: 8%-38%, 20 min) to obtain compound 11-2. $^1$H NMR (400 MHz, DMSO-$d_6$) δ: 13.3 (s, 1H), 8.08 (s, 2H), 7.79-7.82 (m, 1H), 7.57-7.63 (m, 2H). MS m/z: 208 $[M+H]^+$.

Step 2: Synthesis of Compound 11

The hydrochloride of compound 2-4 (50 mg), compound 11-2 (49.69 mg) and N,N-dimethylformamide (1 mL) were added to a reaction flask and stirred, and N,N-diisopropylethylamine (113.95 μL) and HATU (165.84 mg) were added and reacted at 15° C. for 16 h. After the reaction was complete, water was added to the reaction liquid (10 mL), and ethyl acetate (3×10 mL) was used for extraction. The organic phases were combined, dried over anhydrous sodium sulfate, and concentrated under reduced pressure to obtain a crude product. The crude product was purified by preparative HPLC (column: Waters Xbridge BEH C18 100*30 mm*10 m; mobile phase: [water (containing 10 mM $NH_4HCO_3$)-acetonitrile]; acetonitrile %: 20%-50%, 8 min) to obtain compound 11. $^1$H NMR (400 MHz, DMSO-$d_6$) δ: 11.75-12.21 (m, 1H), 7.80-8.24 (m, 3H), 7.69 (dd, J=8.13, 3.25 Hz, 1H), 7.19-7.56 (m, 2H), 6.60-7.14 (m, 2H), 4.66-5.21 (m, 1H), 3.69-3.81 (m, 3H), 3.31 (s, 1H), 3.19 (s, 1H), 2.34-2.42 (m, 1H), 1.72-1.84 (m, 1H), 0.55-1.03 (m, 2H). MS m/z 419 $[M+H]^+$.

Example 12

Compound 12

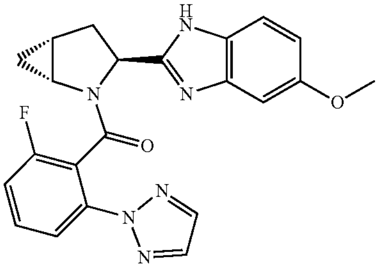

Synthetic Route:

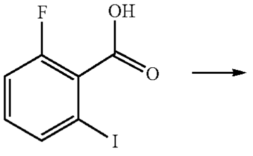

Compound 12-1

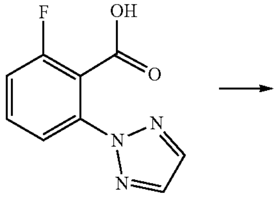

Compound 12-2

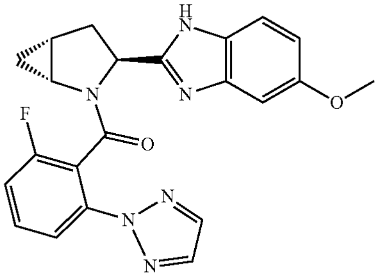

Compound 12

Step 1: Synthesis of Compound 12-2

Compound 12-1 (1 g), 1H-1,2,3-triazole (285.60 mg), cesium carbonate (1.84 g), 1,10-phenanthroline (33.87 mg) and 1,4-dioxane (10 mL) were added to a reaction flask, and cuprous iodide (71.60 mg) was added and reacted at 100° C. for 16 h. After the reaction was complete, water was added to the reaction liquid (10 mL), pH was adjusted to 1-2 with HCl, and ethyl acetate (3×30 mL) was used for extraction. The organic phases were combined, dried over anhydrous sodium sulfate, and concentrated under reduced pressure to obtain a crude product. The crude product was separated and purified by silica gel column chromatography (eluent: DCM: MeOH=100:1 to 50:1) to obtain compound 12-2. $^1$H NMR (400 MHz, DMSO-$d_6$) δ: 13.67 (s, 1H), 8.16 (s, 2H), 7.71-7.80 (m, 1H), 7.68-7.70 (m, 1H), 7.44-7.47 (m, 1H).

Step 2: Synthesis of Compound 12

The hydrochloride of compound 2-4 (50 mg), compound 12-2 (35.08 mg) and acetonitrile (1 mL) were added to a pre-dried one-necked flask and stirred, then reagents N,N-diisopropylethylamine (65.55 μL), N-methylimidazole (52.49 μL), N,N,N,N-tetramethylchloroformamidine hexafluorophosphate (63.35 mg) were added and reacted at 15° C. for 16 h. After the reaction was complete, water was added to the reaction liquid (10 mL), and ethyl acetate (3×10 mL) was used for extraction. The organic phases were combined, dried over anhydrous sodium sulfate, and concentrated under reduced pressure to obtain a crude product. The crude product was purified by preparative HPLC (column: Waters Xbridge BEH C18 100*30 mm*10 m; mobile phase: [water (containing 10 mM $NH_4HCO_3$)-acetonitrile]; acetonitrile %: 20%-50%, 8 min) to obtain compound 12. $^1$H NMR (400 MHz, DMSO-$d_6$) δ: 11.34-12.19 (m, 1H), 8.10-8.29 (m, 1H), 7.63-7.92 (m, 2H), 7.39-7.54 (m, 2H), 6.59-7.37 (m, 3H), 4.52-5.52 (m, 1H), 3.70-3.87 (m, 3H), 3.12-

3.31 (m, 1H), 2.77-2.99 (m, 1H), 2.34-2.63 (m, 1H), 1.74-1.97 (m, 1H), 0.72-1.18 (m, 1.5H), 0.24-0.50 (m, 0.5H). MS m/z: 419 $[M+H]^+$.

Example 13

Compound 13

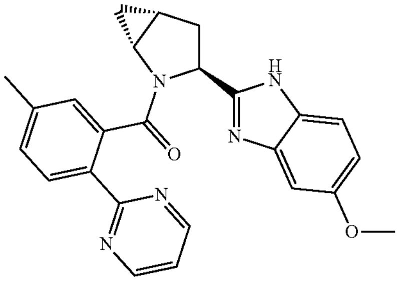

Synthetic Route:

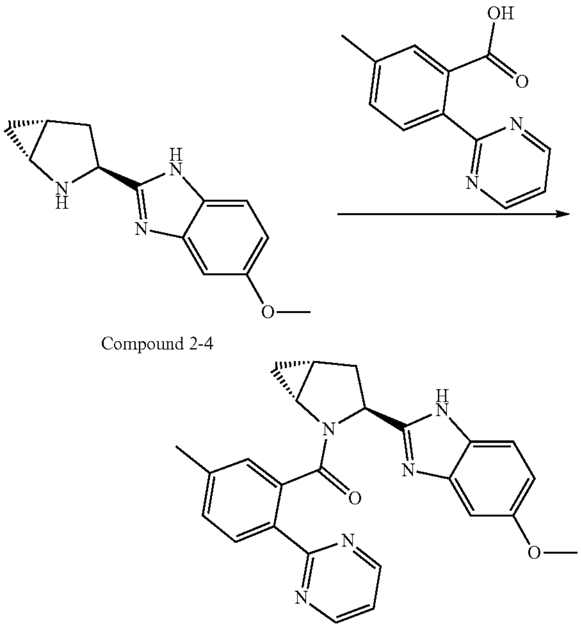

Compound 2-4

Compound 13

Step 1: Synthesis of Compound 13

The hydrochloride of compound 2-4 (30 mg), 5-methyl-2-(pyrimidin-2-yl)benzoic acid (25.23 mg) and tetrahydrofuran (1 mL) were added to a reaction flask and stirred, and triethylamine (91.06 μL) and a solution of tri-n-propylcyclophosphoric anhydride in ethyl acetate (233.45 μL, 50% concentration) were added and reacted at 15° C. for 16 h. After the reaction was complete, water was added to the reaction liquid (10 mL), and ethyl acetate (3×10 mL) was used for extraction. The organic phases were combined, dried over anhydrous sodium sulfate, and concentrated under reduced pressure to obtain a crude product. The crude product was separated and purified by silica gel column chromatography (eluent: petroleum ether:ethyl acetate=1:1 to 0:1) and the obtained product was purified by preparative HPLC (chromatographic column: Waters Xbridge BEH C18 100*30 mm*10 m; mobile phase: [water (containing 10 mM $NH_4HCO_3$)-acetonitrile]; acetonitrile %: 25%-55%, 8 min) to obtain compound 13. $^1H$ NMR (400 MHz, $CDCl_3$) δ: 8.18-8.33 (m, 3H), 7.33-7.62 (m, 2H), 7.28 (s, 1H), 7.04-7.19 (m, 1H), 6.89-7.00 (m, 2H), 5.64 (dd, J=8.82, 2.69 Hz, 1H), 3.88 (s, 3H), 3.57 (m, 1H), 2.81-2.93 (m, 1H), 2.47 (s, 3H), 2.29-2.41 (m, 1H), 1.94-2.04 (m, 1H), 0.69-0.84 (m, 1H), 0.48-0.61 (m, 1H). MS m/z: 426 $[M+H]^+$.

Example 14

Compound 14

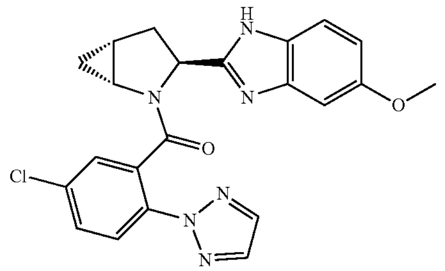

Synthetic Route:

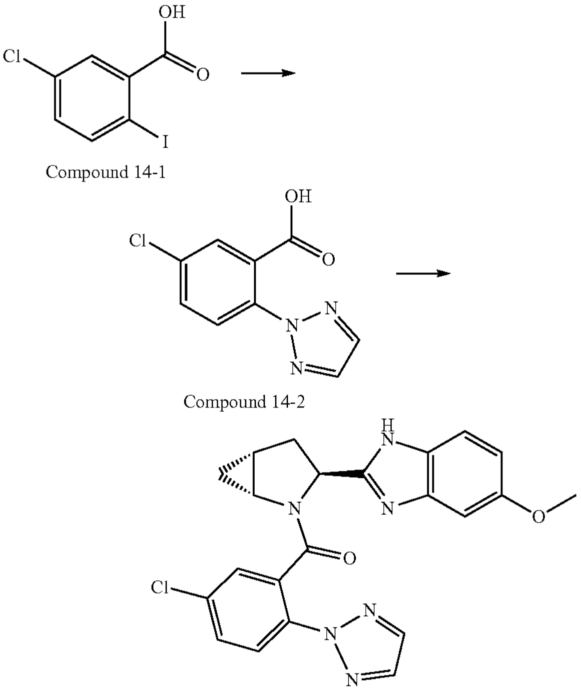

Compound 14-1

Compound 14-2

Compound 14

Step 1: Synthesis of Compound 14-2

Compound 14-1 (9 g), 1H-1,2,3-triazole (2.42 g) and 1,4-dioxane (90 mL) were added to a reaction flask and stirred, and cesium carbonate (15.57 g), 1,10-phenanthroline (287.10 mg) and cuprous iodide (606.82 mg) were added, nitrogen replacement was performed three times and the reaction was performed at 100° C. for 16 h. After the reaction was complete, water was added to the reaction liquid (10 mL), pH was adjusted to 1-2 with HCl, and ethyl acetate (3×100 mL) was used for extraction. The organic phases were combined, dried over anhydrous sodium sulfate, and concentrated under reduced pressure to obtain a crude product. The crude product was separated and purified by silica gel column chromatography (eluent: DCM: MeOH=100:1 to 50:1) to obtain compound 14-2. $^1H$ NMR (400 MHz, DMSO-$d_6$) δ: 13.46 (s, 1H), 8.1 (s, 2H), 7.77-7.82 (m, 3H). MS m/z: 224 $[M+H]^+$.

Step 2: Synthesis of Compound 14

Acetonitrile (1 mL) was added to a reaction flask, and the hydrochloride of compound 2-4 (50 mg), compound 14-2 (43.89 mg), N,N-diisopropylethylamine (75.97 μL), N-methylimidazole (60.84 μL) and N,N,N,N-tetramethylchloroformamidine hexafluorophosphate (73.43 mg) were added at 15° C. under stirring and reacted at 15° C. for 16 h. After the reaction was complete, water was added to the reaction liquid (10 mL), and ethyl acetate (3×10 mL) was used for extraction. The organic phases were combined, dried over anhydrous sodium sulfate, and concentrated under reduced pressure to obtain a crude product. The crude product was purified by preparative HPLC (column: Waters Xbridge BEH C18 100*30 mm*10 m; mobile phase: [water (containing 10 mM $NH_4HCO_3$)-acetonitrile]; acetonitrile %: 30%-60%, 8 min) to obtain compound 14. $^1H$ NMR (400 MHz, $CDCl_3$) δ: 8.03 (d, J=8.63 Hz, 1H), 7.38-7.62 (m, 5H), 7.06-7.18 (m, 1H), 6.96 (dd, J=8.82, 2.31 Hz, 1H), 5.63 (dd, J=8.57, 2.19 Hz, 1H), 3.89 (s, 3H), 3.53 (m, 1H), 2.83 (t, 1H), 2.33 (m, 1H), 1.98-2.10 (m, 1H), 0.78-0.91 (m, 1H), 0.54 (br s, 1H). MS m/z: 435 $[M+H]^+$.

Biological Test

Experimental Example 1: Test of In Vitro Activity of OX1 and OX2 Receptors

Objectives:

The change of intracellular calcium signal was detected by FLIPR, and the antagonism of the compounds on OX1R and OX2R receptors was evaluated by using $IC_{50}$ value of the compounds as an index.

Experimental Materials:

Cell lines: Transfected HEK293-OX1R and HEK293-OX2R stable cell lines

HEK293-OX1R cell culture medium (DMEM, Invitrogen #11960-044, 10% serum Gibco #10099141, L-Glutamine 1×, Gibco #25030, sodium pyruvate 1×, Gibco #11360, Geneticin 300 μg/mL, Gibco #10131)

HEK293-OX2R cell culture medium (DMEM, Invitrogen #11960-044, 10% serum Gibco #10099141, L-Glutamine 1×, Gibco #25030, sodium pyruvate 1×, Gibco #11360, Geneticin 300 μg/mL, Gibco #10131, Blasticin 2 μg/mL, Invitrogen #R21001)

TABLE 1

Reagents, instruments, brands and catalog numbers used

| Reagent/Instrument | Brand and catalog number |
|---|---|
| Trypsin | Invitrogen, #25200-072 |
| DPBS (Dulbecco's phosphate buffered saline) | Hyclone, #SH30028.01B |
| Fluo-4 Direct (fluorescent probe) | Invitrogen, Cat# F10471 |
| F-127 (poloxamer) | Invitrogen #P3000MP |
| Probenecid (probenecid) | Sigma #P8761 |
| 384 cell plate | Greiner #781946 |
| 384 compound plate | Greiner #781280 |
| $CO_2$ incubator | Thermo #371 |
| Centrifuge | Eppendorf #5810R |

TABLE 1-continued

Reagents, instruments, brands and catalog numbers used

| Reagent/Instrument | Brand and catalog number |
|---|---|
| Vi-cell cell counter | Beckman Coulter |
| Labcyte FLIPR | Molecular Device |

POD 810 Plate Assembler Automatic Microplate Pretreatment System

Experimental Steps and Methods:

a) Cell seeding (HEK293-OX1R and HEK293-OX2R cells)

1) preheating the culture medium, trypsin and DPBS under water bath at 37° C.; pipetting and removing the medium of cell culture and washing same with 10 mL of DPBS;

2) adding the preheated trypsin to a culture flask, rotating the culture flask so that the trypsin evenly covered the culture flask, and putting the culture flask in a 37° C., 5% $CO_2$ incubator for digestion for 1-2 min;

3) suspending the cells with 10-15 mL of medium for each T150 and centrifuging at 800 rpm for 5 min; resuspending the cells with 10 mL of medium, pipetting 1 mL of the cell suspension and counting with Vi-cell;

4) diluting OX1R cells with medium to $5\times10^5$ cells/mL, and diluting OX2R cells with medium to $4\times10^5$ cells/mL, and adding the diluted cells to 384 plate (Greiner.781946) with a multi-channel pipette (50 μL/well, 25000 cells/well for OX1R cells, 20000 cells/well for OX2R cells); placing the cell plate in a 37° C., 5% $CO_2$ incubator overnight.

b) Compound loading:

1) diluting the compound to 20 mM with DMSO, 3-fold dilution, 8 gradients, duplicate wells, and adding same to a compound plate with an Echo liquid handler; then adding 20 μL of buffer to maintain the final concentration of DMSO of 0.1%.

c) FLIPR experiment:

1) washing off the cell culture medium in the 384 plate with a vacuum pump, adding L of Fluo-4 Direct fluorescent dye, incubating in 37° C., 5% $CO_2$ incubator for 1 h, and balancing at room temperature for another 10 min.

2) $EC_{50}$ test: manually diluting Orexin A on ice, 3-fold dilution, 8 gradients, duplicate wells; preparing a DMSO plate and keep the DMSO concentration to be 0.5%; putting the cell plate, OrexinA plate, and DMSO plate in FLIPR respectively, and reading the fluorescence value.

3) calculating the $EC_{70}$ value based on the $EC_{50}$ value of Orexin A; preparing a $5\times EC_{70}$ solution, adding same to 384 compound plate with a multi-channel pipette, and storing on ice;

4) putting the compound plate, $5\times EC_{70}$ plate, cell plate, and FLIPR tip in sequence in FLIPR, running the program, and reading the fluorescence value.

d) Data analyzing: using Prism5.0 to analyze the data, and calculating the $IC_{50}$ value of the compound.

The experimental results are shown in Table 2:

TABLE 2

| Test results of $IC_{50}$ by FLIPR detection | | |
|---|---|---|
| Compound No. | hOXIR $IC_{50}$ (nM) | hOX2R $IC_{50}$ (nM) |
| Compound 1 | >10000 | 25 |
| Compound 2 | >10000 | 72 |
| Compound 4 | 462 | 64 |
| Compound 5 | 337 | 96 |
| Compound 6 | 1416 | 299 |
| Compound 7 | 877 | 24 |
| Compound 8 | 1794 | 42 |
| Compound 9 | 3170 | 42 |
| Compound 10 | 710 | 17 |
| Compound 11 | 3602 | 33 |
| Compound 12 | 1278 | 81 |
| Compound 13 | 2444 | 60 |
| Compound 14 | 1036 | 30 |

Conclusion: The compound of the present disclosure has a certain antagonistic activity on human orexin receptors, and exhibits higher activity on OX2 receptors.

Experimental Example 2: Determination of Pharmacokinetic Parameters of Test Substances in SD Rat Plasma 4 healthy male SD rats aged 6-9 weeks were selected and randomly divided into two groups, with 2 rats in each group. One group was given the test compound at 2 mg/kg by intravenous injection, and the other group was given the test compound at 10 mg/kg by intragastric administration. Plasma samples were collected at 0.083, 0.25, 0.5, 1.0, 2.0, 4.0, 6.0, 8.0, and 24 h after administration for the intravenous injection group and intragastric administration group, respectively. Quantitative analysis of all biological samples was carried out by LC-MS/MS method, and the WinNonlin™ Version 6.3 (Pharsight, Mountain View, CA) pharmacokinetic software was used to calculate the relevant pharmacokinetic parameters by the non-compartmental model linear logarithmic trapezoidal method. $AUC_{0\text{-}last}$ represents area under the plasma concentration-time curve from time zero to the last detectable concentration time point; p.o. represents oral; i.v. represents intravenous injection; $T_{1/2}$ represents half-life; CL represents clearance rate; Vd represents apparent volume of distribution; $C_{max}$ represents peak concentration; $T_{max}$ represents time to peak; F % represents oral bioavailability. The experimental results are shown in Table 3.

TABLE 3

| Pharmacokinetic properties of the test compound | | |
|---|---|---|
| PK parameter | | Compound 8 |
| i.v. 2 mg/kg | $T_{1/2}$ (h) | 0.2 |
| | $Vd_{ss}$ (L/kg) | 0.57 |
| | CL (mL/min/kg) | 44 |
| | $AUC_{0\text{-}last}$ (nM · h) | 1761 |
| p.o. 10 mg/kg | $T_{max}$ (h) | 0.25 |
| | $C_{max}$ (nM) | 1032 |
| | $AUC_{0\text{-}last}$ (nM · h) | 1451 |
| | F % | 17% |

Conclusion: The compound of the present disclosure exhibits good pharmacokinetic properties in SD rats.

Experimental Example 3: Determination of Drug Concentration of Test Substance in Brain Tissue of SD Rats 4 healthy male SD rats aged 6-9 weeks were selected and given the test compound by intragastric administration. 2 animals were randomly selected to be euthanized at 0.5 h and 2 h after administration, respectively. Plasma and brain tissue samples were collected, and LC-MS/MS method was used for quantitative analysis of all biological samples. The experimental results are shown in Table 4.

TABLE 4

| Brain-to-blood ratio of test compound in rats | | | |
|---|---|---|---|
| | | Compound 8 (0.5 h) | Compound 8 (2 h) |
| p.o. 30 mg/kg | Drug concentration in brain (nmol/L) | 1393 | 212 |
| | Drug concentration in plasma (nmol/L) | 5600 | 1100 |
| | Brain-to-blood ratio | 0.25 | 0.19 |

Conclusion: The compound of the present disclosure can penetrate the blood-brain barrier and enter the brain tissue in rats.

Experimental Example 4: Determination of Free Drug Ratio of Test Substance in Brain Tissue of SD Rats The brain tissue homogenate of SD rats (that is, matrix, purchased from BioIVT) was taken, and the DMSO working solution of the test compound or the DMSO working solution of a control (propranolol) was added, so that the final concentrations of the test compound and propranolol in the plasma samples were both 2 μM, and the samples were fully mixed. The final concentration of DMSO was controlled to be 0.5%; 50 μL was pipetted into a sample receiving plate, and a corresponding volume of corresponding blank matrix/buffer was immediately added so that the final volume of each sample well was 100 μL, and the volume ratio of matrix:dialysis buffer was 1:1, and then a stop solution was added to these samples. This sample would be used as a $T_0$ sample for recovery rate and stability determination. The test compound sample and propranolol sample were added to the administration end of each dialysis well, and blank dialysis buffer was added to the corresponding receiving end of the dialysis well. Then the plate was placed in a humidified 5% $CO_2$ incubator and incubated for 4 h at 37° C. with shaking at 100 rpm. After dialysis, 50 μL of the dialyzed buffer sample and the dialyzed brain tissue homogenate sample was pipetted to a new sample receiving plate, respectively. A corresponding volume of corresponding blank matrix/buffer was added to the samples so that the final volume of each sample well was 100 μL and the volume ratio of plasma:dialysis buffer was 1:1. All samples were analyzed by LC/MS/MS after protein precipitation, and the free rate (% Unbound), binding rate (% Bound) and recovery rate (% Recovery) of the compound were calculated by the following formula:

$$\% \text{ Unbound} = 100 * F_C/T_C,$$

$$\% \text{ Bound} = 100 - \% \text{ Unbound},$$

$$\% \text{ Recovery} = 100 * (F_C + T_C)/T_0.$$

Among them, $F_C$ is the concentration of the compound at the buffer end of the dialysis plate; $T_C$ is the concentration of the compound at the matrix end of the dialysis plate; $T_0$ is the concentration of the compound in the plasma sample at time zero. The experimental results are shown in Table 5.

TABLE 5

| Test results of binding rate in SD rat brain tissue | |
|---|---|
| Compound No. | SD rat brain tissue_Unbound (%) |
| Compound 8 | 21.8% |

Conclusion: The compound of the present disclosure has a higher proportion of unbound drugs in the SD rat brain tissue.

Experimental Example 5: Determination of Pharmacokinetic Parameters of Test Substance in Beagle Dog Plasma 4 healthy male Beagle dogs were selected and randomly divided into two groups, with 2 dogs in each group. One group was given the test compound at 1 mg/kg by intravenous injection, and the other group was given the test compound at 5 mg/kg by intragastric administration. Plasma samples were collected at 0.033, 0.083, 0.25, 0.5, 1.0, 2.0, 4.0, 6.0, 8.0, and 24 h after administration for the intravenous injection group and intragastric administration group, respectively. Quantitative analysis of all biological samples was carried out by LC-MS/MS method, and the WinNonlin™ Version 6.3 (Pharsight, Mountain View, CA) pharmacokinetic software was used to calculate the relevant pharmacokinetic parameters by the non-compartmental model linear logarithmic trapezoidal method. $AUC_{0\text{-}last}$ represents area under the plasma concentration-time curve from time zero to the last detectable concentration time point; p.o. represents oral; i.v. represents intravenous injection; $T_{1/2}$ represents half-life; CL represents clearance rate; Vd represents apparent volume of distribution; $C_{max}$ represents peak concentration; $T_{max}$ represents time to peak; F % represents oral bioavailability. The experimental results are shown in Table 6.

TABLE 6

| Pharmacokinetic properties of test compound | | |
|---|---|---|
| PK parameter | | Compound 8 |
| i.v. 1 mg/kg | $T_{1/2}$ (h) | 2.79 |
| | $Vd_{ss}$ (L/kg) | 0.41 |
| | CL (mL/min/kg) | 2.57 |
| | $AUC_{0\text{-}last}$ (nM · h) | 15320 |
| p.o. 5 mg/kg | $T_{max}$ (h) | 1 |
| | $C_{max}$ (nM) | 6180 |
| | $AUC_{0\text{-}last}$ (nM · h) | 26182 |
| | F % | 34% |

Conclusion: The compound of the present disclosure exhibits good pharmacokinetic properties in Beagle dogs.

Experimental Example 6: Determination of Drug Concentration of Test Substance in Cerebrospinal Fluid of Beagle Dogs 2 healthy male Beagle dogs were selected, and after intragastric administration of the test compound at 5 mg/kg, cerebrospinal fluid samples were taken at 0.5 h, 2 h and 6 h after the administration, respectively. Quantitative analysis of all biological samples was carried out by LC-MS/MS method, and the WinNonlin™ Version 6.3 (Pharsight, Mountain View, CA) pharmacokinetic software was used to calculate the relevant pharmacokinetic parameters by the non-compartmental model linear logarithmic trapezoidal method. $AUC_{0\text{-}last}$ represents area under the plasma concentration-time curve from time zero to the last detectable concentration time point; p.o. represents oral; i.v. represents intravenous injection; $T_{1/2}$ represents half-life; CL represents clearance rate; Vd represents apparent volume of distribution; $C_{max}$ represents peak concentration; $T_{max}$ represents time to peak; F % represents oral bioavailability. The experimental results are shown in Table 7.

TABLE 7

| Drug concentration of test compound in canine cerebrospinal fluid | | | | |
|---|---|---|---|---|
| | | Compound 8 (0.5 h) | Compound 8 (2 h) | Compound 8 (6 h) |
| p.o. 5 mg/kg | Drug concentration in cerebrospinal fluid (nmol/L) | 1160 | 773 | 110 |

Conclusion: The compound of the present disclosure can be detected in dog CSF, indicating that the compound can pass through the blood-brain barrier and reach the brain.

Experimental Example 7: Effect of Test Substance on Spontaneous Activities of SD Rats Test purpose: to judge the effect of the test compound on the activity of rats by measuring the spontaneous activity distance of rats in a period of time.

Test scheme: 12 male SD rats aged 7 weeks were adapted in the laboratory 1 day before the start of the test. On the day of the experiment, the rats were randomly divided into 2 groups according to their body weight, with 6 rats in each group, and the rats were given blank vehicle and compound 8 (30 mg/kg), respectively. The animals were put into a test box 30 minutes after administration, and the distance data of animal activity were recorded every 5 min with Any-maze software, and the recording was continued for 60 min. By comparing the total distance of animal activity within the recording time, it is judged whether the drug has a significant effect on the spontaneous activity of the animal. The experimental data were represented by the mean±standard deviation (Mean±SEM). The statistical method adopted one-way analysis of variance plus Dunnett's multiple comparisons. $P<0.05$ was represented as *, $p<0.01$ was represented as , and $p<0.001$ was represented as *. The experimental results are shown in Table 8.

TABLE 8

| Test data of rat spontaneous activity | | |
|---|---|---|
| Group | Spontaneous activity distance | Statistical analysis result |
| Blank vehicle | 31.91 ± 3.92 meters | |
| Compound 8 at 30 mg/kg | 14.73 ± 1.38 meters | — |

Conclusion: The compound of the present disclosure can significantly reduce the spontaneous activity distance of SD rats.

Experimental Example 8: Evaluation of the Effect of Test Substance on Sleep in SD Rats by Electroencephalogram/Electromyography Telemetry Test purpose: to evaluate the effect of test substance on sleep in SD rats by electroencephalogram/electromyography telemetry (EEG).

Test scheme: 36 male SD rats aged 5-6 weeks needed an adaptation period of 5-15 days after arriving at the facility, during which the experimental animals were placed in an alternating light and dark environment for 12 h for adaptation (light on: 19:00; light off: 07:00) to adjust the rhythm time, and the health of the animals was monitored every day. Animals needed to be surgically implanted with electroencephalogram electrode and electromyography electrode for later telemetry data collection. On the day of the operation experiment, the animals were anesthetized with Zoletil (i.p., 20 mg/kg) combined with xylazine (i.p., 8 mg/kg). After anesthesia, the animals were fixed by brain stereotaxic apparatus. After the head has hair clipped and was disinfected, the skin of the head was cut, and the four corners were clamped with hemostats to fully expose the skull. The periosteum was peeled off and wiped with dry absorbent cotton until the surface was clean. A hole was drilled according to the type of implanter, and an electrode was implanted and in contact with the dura mater. The electrode was fixed on the skull with dental cement. At the same time, the cement dripping on the tissue and skin was cleaned up. The 2 electromyography electrodes were respectively inserted into the neck muscles in parallel, and the two ends were fixed with sutures to prevent their ends from touching each other. The implanter was then placed under the skin, and the surgical wound was sutured and sterilized. After the operation, the rats were carefully placed in a clean recovery cage, lying on their sides to ensure a smooth airway. The rats were raised in a single cage and placed in a shielded recovery room, in which the light and dark automatically alternated for 12 h (light on: 19:00, light off: 07:00), the temperature was 20-26° C., and the relative humidity was 40-70%. After the operation, the animals were given nursing care for 3 days. The surgical incision was treated with cephradine powder locally, gentamicin at 4-8 mg/kg was subcutaneously administered, and meloxicam at 0.1 mL/rat was injected subcutaneously for 3 consecutive days. The experiment was carried out after 7-10 days of recovery and the animals were randomly divided into groups according to their weight the day before the experiment.

On the day of the experiment, the basic electroencephalogram and electromyography were recorded first, and then the administration began. During and after the administration, the electroencephalogram and electromyography were recorded continuously until 24 h after the administration. Raw data were collected by DSI system Ponemah software and analyzed by NeuroScore software. The experimental data were represented by the mean±standard error (Mean±SEM), and statistical analysis was performed using the one-way variance method. Compared with the blank vehicle group, $P<0.05$ indicated a significant difference, and represented as *; $P<0.01$ indicated a very significant difference, and represented as ; $P<0.001$ indicated an extremely significant difference, and represented as *. The experimental results are shown in Table 9.

TABLE 9

| Rat EEG test data | | | |
|---|---|---|---|
| Group | Sleep latency (min) | Total awake time within 7 h after administration (min) | NREM sleep time within 7 h after administration (min) |
| Blank vehicle group | 32 ± 3.1 | 303 ± 20 | 102 ± 18 |
| Compound 8 at 5 mg/kg | 27 ± 8.1 | 274 ± 19 | 129 ± 17 |
| Compound 8 at 10 mg/kg | 15 ± 2.9** | 250 ± 21 | 144 ± 16 |
| Compound 8 at 30 mg/kg | 7 ± 1.3*** | 228 ± 12* | 171 ± 11** |

Conclusion: the compound of the present disclosure at 10 mg/kg and 30 mg/kg can significantly shorten the sleep latency of SD rats, and the compound of the present disclosure at 30 mg/kg can significantly reduce the awake time and increase the sleep time within 7 h after administration. Therefore, the compound of the present disclosure has good sleep-promoting drug effect.

What is claimed is:

1. A compound represented by formula (I) or a pharmaceutically acceptable salt thereof:

(I)

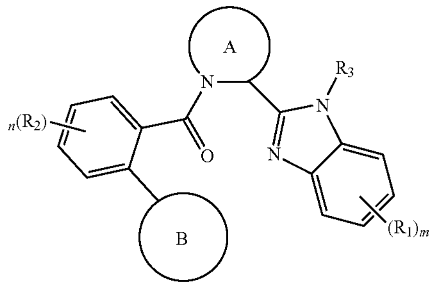

wherein each $R_1$ is independently selected from halogen, cyano, $C_{1-3}$alkyl and $C_{1-3}$alkoxy, and the $C_{1-3}$alkyl and $C_{1-3}$alkoxy are each independently and optionally substituted by 1, 2 or 3 halogen atoms;

each $R_2$ is independently selected from halogen, cyano, $C_{1-3}$alkyl and $C_{1-3}$alkoxy, and the $C_{1-3}$alkyl and $C_{1-3}$alkoxy are each independently and optionally substituted by 1, 2 or 3 halogen atoms;

$R_3$ is selected from H, $C_{1-3}$alkyl and $C_{3-6}$cycloalkyl;

m and n are each independently selected from 0, 1, 2 and 3;

ring A is selected from

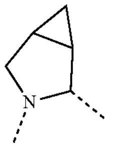

and

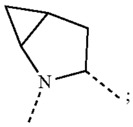

ring B is selected from

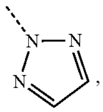

,

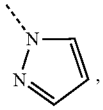

,

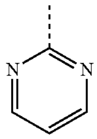

and

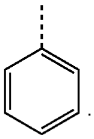

.

2. The compound or the pharmaceutically acceptable salt thereof according to claim 1, wherein each $R_1$ is independently selected from halogen, cyano, methyl and methoxy, and the methyl and methoxy are each independently and optionally substituted by 1, 2 or 3 F.

3. The compound or the pharmaceutically acceptable salt thereof according to claim 2, wherein each $R_1$ is independently selected from F, Cl, methyl and methoxy.

4. The compound or the pharmaceutically acceptable salt thereof according to claim 1, wherein each $R_2$ is independently selected from halogen, cyano, methyl and methoxy, and the methyl and methoxy are each independently and optionally substituted by 1, 2 or 3 F.

5. The compound or the pharmaceutically acceptable salt thereof according to claim 4, wherein each $R_2$ is independently selected from F, Cl, methyl and methoxy.

6. The compound or the pharmaceutically acceptable salt thereof according to claim 1, wherein $R_3$ is selected from H, methyl and cyclopropyl.

7. The compound or the pharmaceutically acceptable salt thereof according to claim 1, wherein the compound is selected from structures shown in formulas (I-1), (I-2) and (I-3),

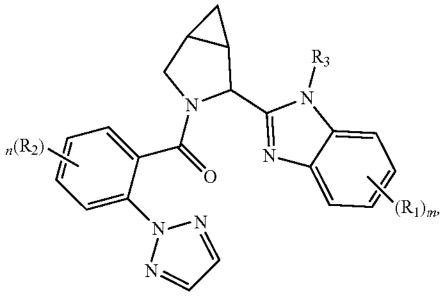

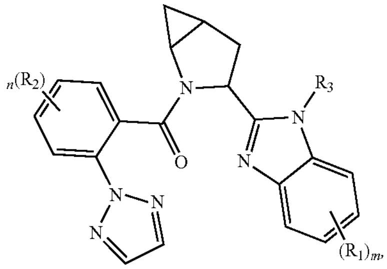

and

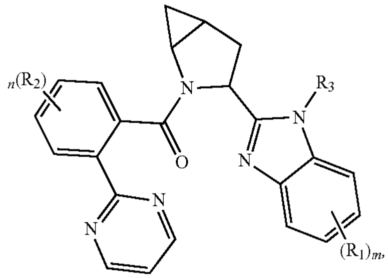

wherein $R_1$, $R_2$, $R_3$, m and n are as defined in claim 1.

8. A compound represented by the following formula or a pharmaceutically acceptable salt thereof, wherein the compound is selected from:

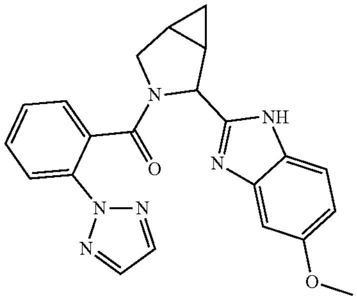

,

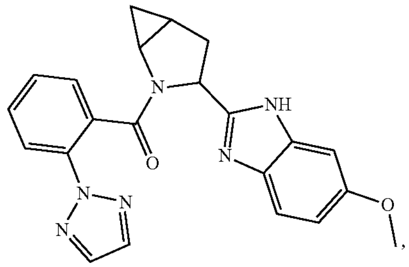

,

-continued
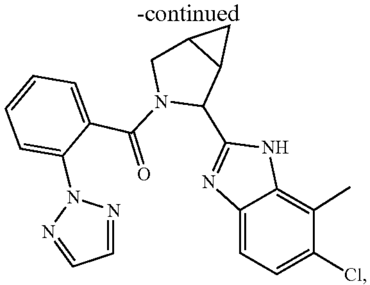
,
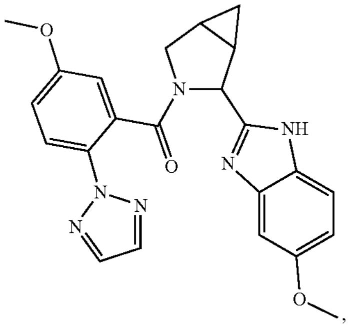
,
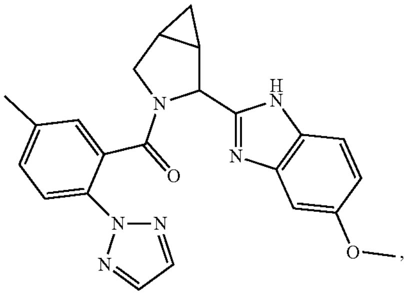
,
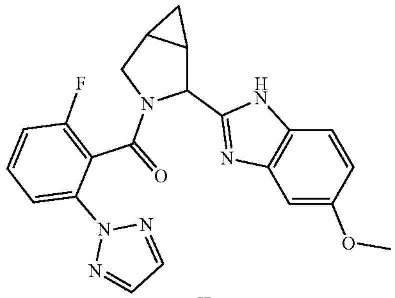
,
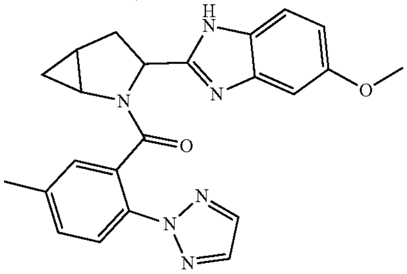
,
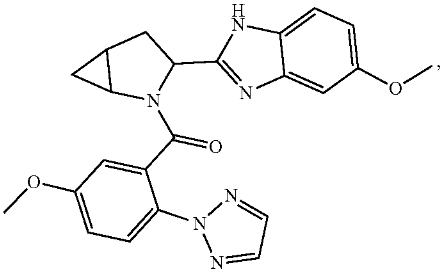
,
-continued
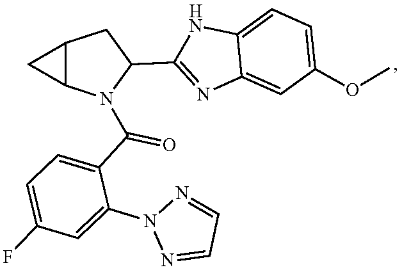
,
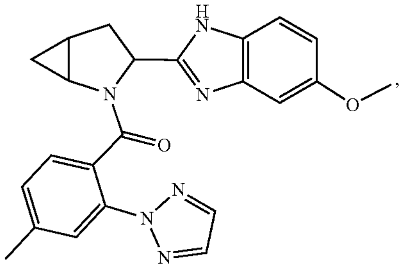
,
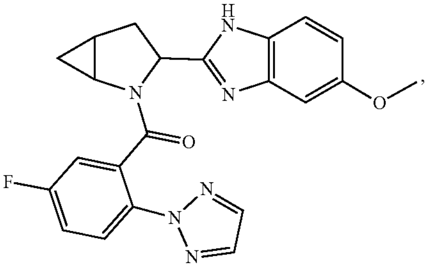
,
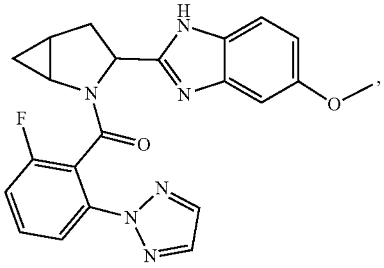
,
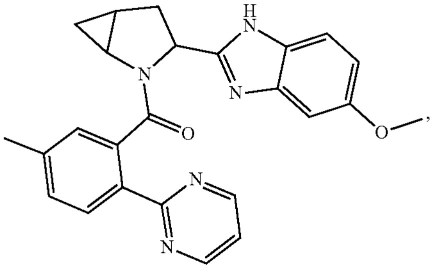
, and
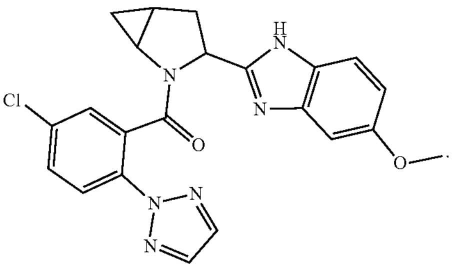
.
9. The compound or the pharmaceutically acceptable salt thereof according to claim 8, wherein the compound is selected from:

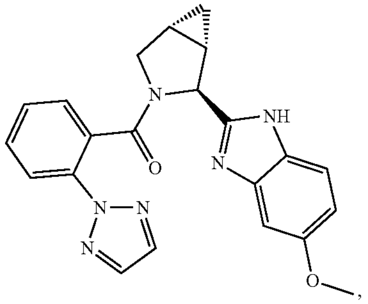,
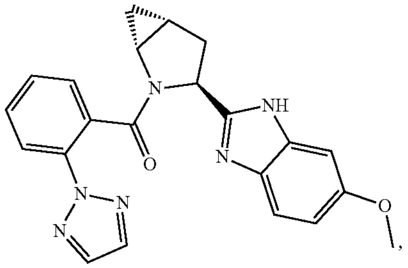,
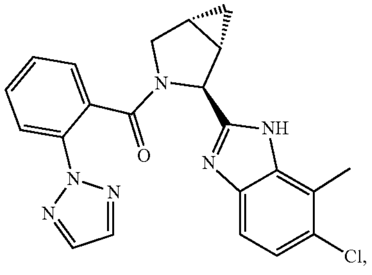,
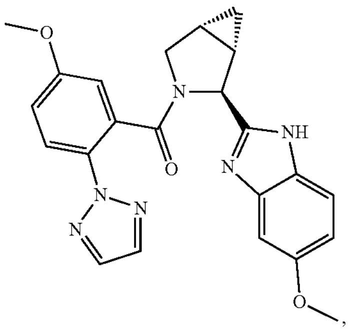,
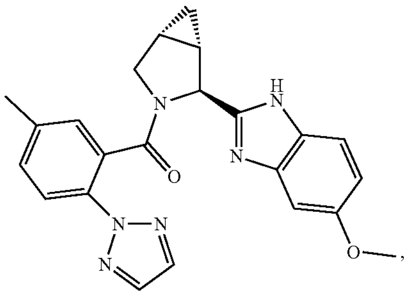,
-continued
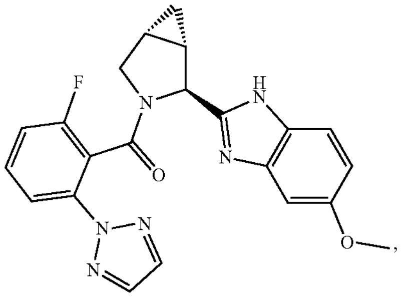,
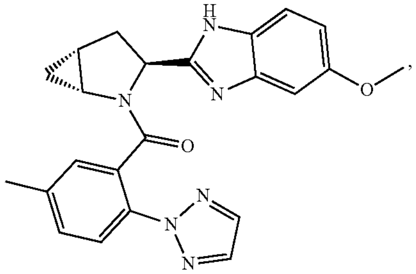,
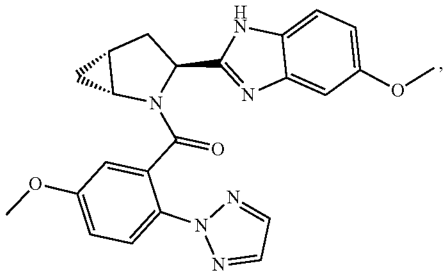,
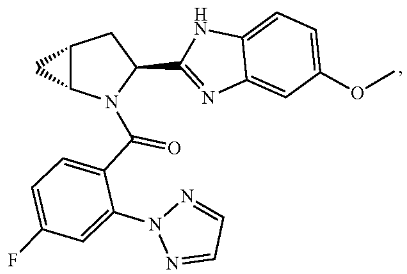,
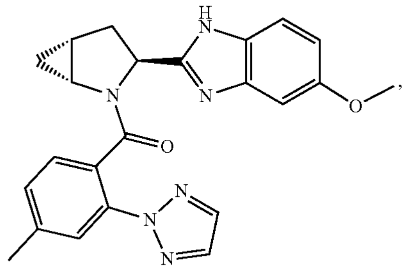,
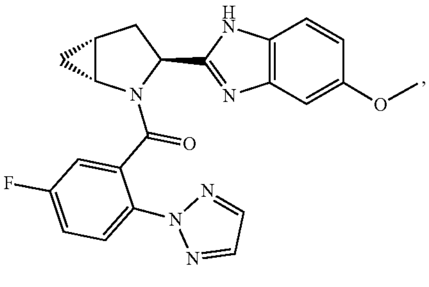, -continued

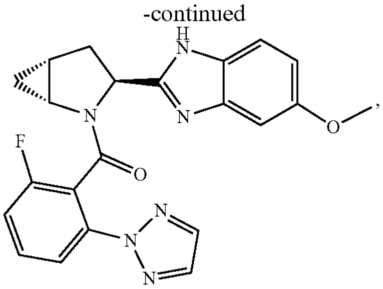

,

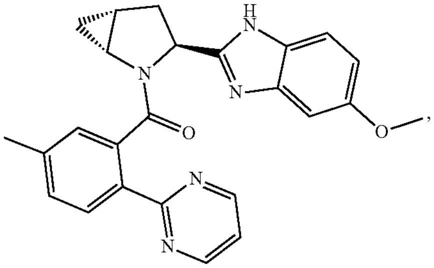

, and

-continued

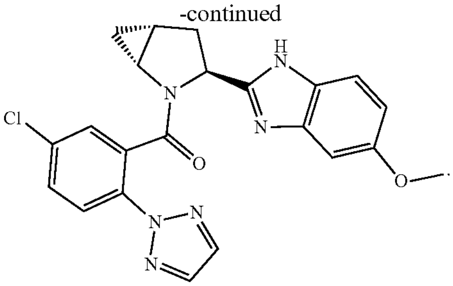

.

10. A method for treating a disease related to a selective orexin-2 receptor antagonist in a subject in need thereof, comprising: administering the compound or the pharmaceutically acceptable salt thereof according to claim 1 to the subject.

11. The method according to claim 10, wherein the disease related to the selective orexin-2 receptor antagonist is selected from insomnia and depression.

* * * * *